US012662665B2

(12) United States Patent
Ringel et al.

(10) Patent No.: US 12,662,665 B2
(45) Date of Patent: Jun. 23, 2026

(54) MODIFIED TERPENE SYNTHASES AND THEIR USE FOR PRODUCTION OF PSEUDOPTEROSIN INTERMEDIATES AND/OR PSEUDOPTEROSINS

(71) Applicant: TECHNISCHE UNIVERSITÄT MÜNCHEN, Munich (DE)

(72) Inventors: Marion Ringel, Munich (DE); Thomas Brück, Eichenried (DE); Markus Reinbold, Augsburg (DE); Daniel Garbe, Unterfohring (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 552 days.

(21) Appl. No.: 18/013,358

(22) PCT Filed: Jul. 2, 2021

(86) PCT No.: PCT/EP2021/068363

§ 371 (c)(1),
(2) Date: Dec. 28, 2022

(87) PCT Pub. No.: WO2022/003167

PCT Pub. Date: Jan. 6, 2022

(65) Prior Publication Data

US 2023/0279377 A1 Sep. 7, 2023

(30) Foreign Application Priority Data

Jul. 2, 2020 (EP) .................................... 20183732

(51) Int. Cl.
*C12N 9/88* (2006.01)
*C12P 5/00* (2006.01)

(52) U.S. Cl.
CPC ................ *C12N 9/88* (2013.01); *C12P 5/005* (2013.01); *C12P 5/007* (2013.01)

(58) Field of Classification Search
CPC .......... C12N 9/88; C12P 5/007; C12Y 402/03
See application file for complete search history.

(56) References Cited

U.S. PATENT DOCUMENTS

2023/0279377 A1* 9/2023 Ringel .................... C12P 5/007 435/166

FOREIGN PATENT DOCUMENTS

| | | | |
|---|---|---|---|
| EP | 3034610 | A1 | 6/2016 |
| WO | 03065001 | A2 | 8/2003 |

OTHER PUBLICATIONS

Cane, David E. et al. "Trichodiene Sythase. Identification of Active Site Residues by Site-Directed Mutagenesis." Biochemistry 34(8):2480-2488, (Year: 1995).
Driller, Ronja et al. "Towards a comprehensive understanding of the structural dynamics of a bacterial diterpene synthase during catalysis." Nature Communications 9(1):1-8, (Year: 2018).
Janke, Ronja et al. "The first structure of a bacterial diterpene cyclase: CotB2." Acta Cryst. 70(6):1528-1537, (Year: 2014).
Tomita, Takeo et al. "Structural Insights into the CotB2-Catalyzed Cyclization of Geranylgeranyl Diphosphate to the Diterpene Cyclooctat-9-en-7-ol." ACS Chem. Biol. 12(6):1621-1628, (Year: 2017).
Yamada, Yuuki et al. "Novel terpenes generated by heterologous expression of bacterial terpene synthase genes in an engineered Streptomyces host." The Journal of Antibiotics 68(6):385-394, Jan. 21, 2015.
Yamada, Yuuki et al. "Terpene synthases are widely distributed in bacteria." PNAS 112(3):857-862, Jan. 20, 2015.
Kohl, Amber C. and Kerr, Rrussell G. "Pseudopterosin Biosynthesis: Aromatization of the Diterpene Cyclase Product, Elisabethatriene," Marine Drugs vol. 1, pp. 54-65, Mar. 2003.

* cited by examiner

*Primary Examiner* — Tekchand Saidha
(74) *Attorney, Agent, or Firm* — SALIWANCHIK, LLOYD & EISENSCHENK

(57) ABSTRACT

The present invention pertains to novel modified terpene synthases and their use for a preparation method for pseudopterosin intermediates and/or pseudopterosins. The method is based on the use of a modified terpene synthase comprising at least one modified amino acid residue, which enables a terpene synthase-catalyzed increased production of pseudopterosin intermediates and/or pseudopterosins from Geranylgeranyl pyrophosphate as starting material. The new modified terpene synthases of this invention allow the production of pseudopterosin intermediates, such as Isoelisabethatriene A, Isoelisabethatriene B, Erogorgiaene, or Seco-Pseudopterosin and/or the production of pseudopterosins, such as Pseudopterosin A, in a cost-efficient, economical, and sustainable manner. Also provided are nucleic acids, encoding for the modified terpene synthases of this invention, as well as expression vectors capable of expressing such nucleic acids and host cells comprising the same.

7 Claims, 15 Drawing Sheets

Specification includes a Sequence Listing.

A elisabethatriene

B isoelisabethatriene A erogorgiaene seco-pseudopterosin pseudopterosin

| Motif | Function | CotB2 | HpS |
|---|---|---|---|
| **D**DXX**D** | Metal ($Mg^{2+}$) binding<br>Diphosphate coordination | DDMD | DDRAID |
| NSE triad<br>((**N**,**D**)D(L,I,V)X(**S**,<br>**T**)XXX**E**) | Metal ($Mg^{2+}$) binding<br>Diphosphate coordination | NDFYSYDRE | NDLXSFARE |
| WXXXXXRY | active site closure by salt<br>bridge formation | WTTSNKRY | WSARSARY |

| | WT | M300I | M304C | M75F | M71Y | M75L |
|---|---|---|---|---|---|---|
| isoelisabethatriene A | 12% | 1% | 9% | 20% | 25% | 44% |
| isoelisabethatriene B | 9% | 17% | 27% | 41% | 16% | 24% |
| hydropyrene | 52% | 48% | 42% | 34% | 35% | 26% |
| hydropyrenol | 26% | 34% | 22% | 5% | 24% | 6% |

Fig. 5 cont.

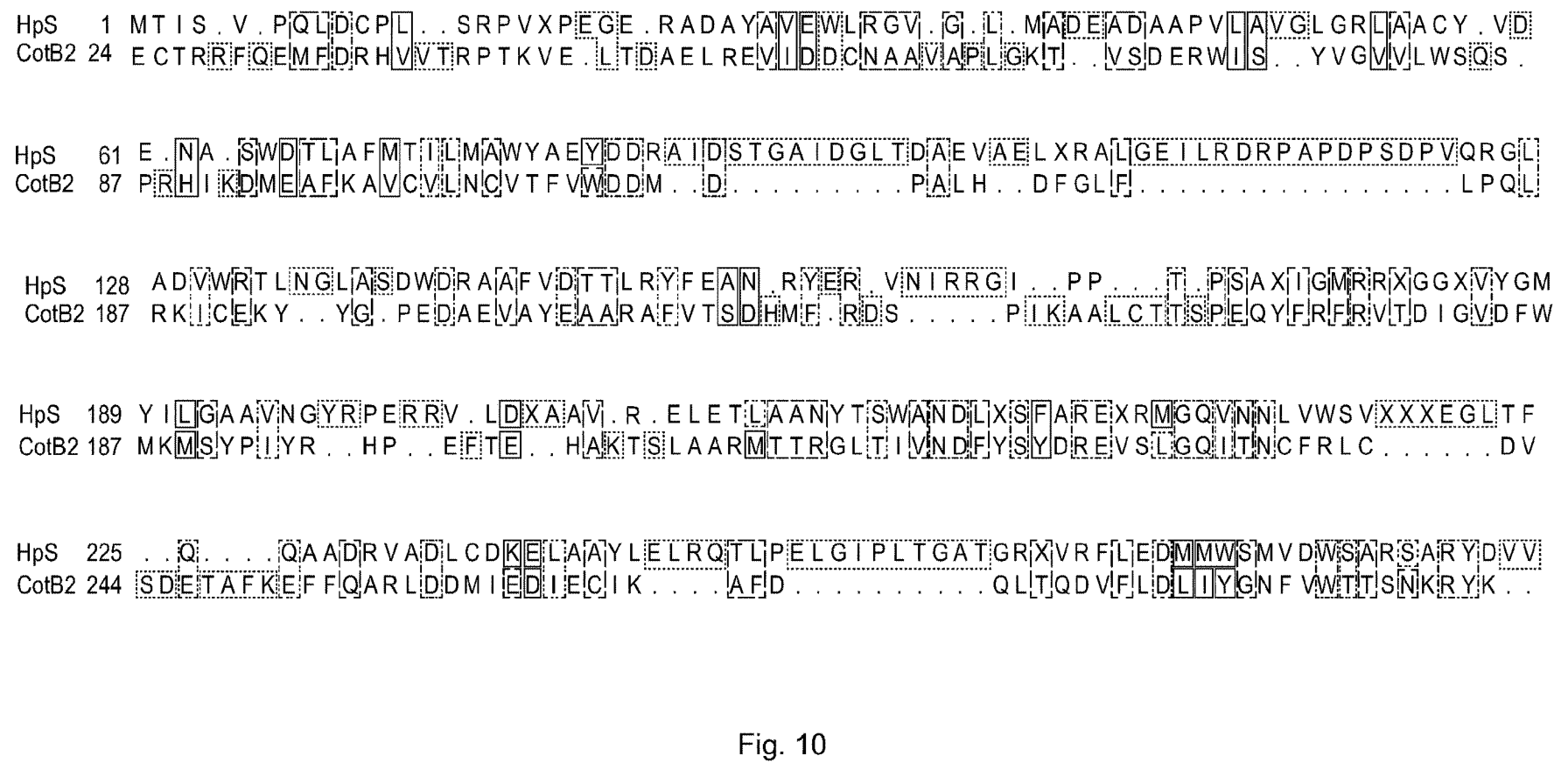

geranylgeranyl diphosphate elisabethatriene elisabethatrienol erogorgiaene hydroxy-erogorgiaene dihydroxy-erogorgiaene seco-pseudopterosin amphilectosin pseudopterosin HpS 1 M T I S . V . P Q L D C P L . . S R P V X P E G E . R A D A Y A V E W L R G V . G . L . M A D E A D A A P V L A V G L G R L A A C Y . V D
CotB2 24 E C T R R F Q E M F D R H V V T R P T K V E . L T D A E L R E V I D D C N A A V A P L G K T . . V S D E R W I S . . Y V G V V L W S Q S .

HpS 61 E . N A . S W D T L A F M T I L M A W Y A E Y D D R A I D S T G A I D G L T D A E V A E L X R A L G E I L R D R P A P D P S D P V Q R G L
CotB2 87 P R H I K D M E A F K A V C V L N C V T F V W D D M . . D . . . . . . . . . . P A L H . . D F G L F . . . . . . . . . . . . . . . . . L P Q L

HpS 128 A D V W R T L N G L A S D W D R A A F V D T T L R Y F E A N . R Y E R . V N I R R G I . . P P . . . T . P S A X I G M R R X G G X V Y G M
CotB2 187 R K I C E K Y . . Y G . P E D A E V A Y E A A R A F V T S D H M F . R D S . . . . . P I K A A L C T T S P E Q Y F R F R V T D I G V D F W

HpS 189 Y I L G A A V N G Y R P E R R V . L D X A A V . R . E L E T L A A N Y T S W A N D L X S F A R E X R M G Q V N N L V W S V X X X E G L T F
CotB2 187 M K M S Y P I Y R . . H P . . E F T E . . H A K T S L A A R M T T R G L T I V N D F Y S Y D R E V S L G Q I T N C F R L C . . . . . . D V

HpS 225 . . Q . . . . Q A A D R V A D L C D K E L A A Y L E L R Q T L P E L G I P L T G A T G R X V R F L E D M M W S M V D W S A R S A R Y D V V
CotB2 244 S D E T A F K E F F Q A R L D D M I E D I E C I K . . . . A F D . . . . . . . . . . Q L T Q D V F L D L I Y G N F V W T T S N K R Y K . .

Fig. 10

SEQUENCE LISTING

```
<160> NUMBER OF SEQ ID NOS: 28

<210> SEQ ID NO 1
<211> LENGTH: 321
<212> TYPE: PRT
<213> ORGANISM: Streptomyces clavuligerus

<400> SEQUENCE: 1

Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60
```

Trp Asp Thr Leu Ala Phe Met Thr Ile Leu Met Ala Trp Tyr Ala Glu
65 70 75 80

Tyr Asp Asp Arg Ala Ile Asp Ser Thr Gly Ala Ile Asp Gly Leu Thr
85 90 95

Asp Ala Glu Val Ala Glu Leu His Arg Ala Leu Gly Glu Ile Leu Arg
100 105 110

Asp Arg Pro Ala Pro Asp Pro Ser Asp Pro Val Gln Arg Gly Leu Ala
115 120 125

Asp Val Trp Arg Thr Leu Asn Gly Leu Ala Ser Asp Trp Asp Arg Ala
130 135 140

Ala Phe Val Asp Thr Thr Leu Arg Tyr Phe Glu Ala Asn Arg Tyr Glu
145 150 155 160

Arg Val Asn Ile Arg Arg Gly Ile Pro Pro Thr Pro Ser Ala His Ile
165 170 175

Gly Met Arg Arg His Gly Gly His Val Tyr Gly Met Tyr Ile Leu Gly
180 185 190

Ala Ala Val Asn Gly Tyr Arg Pro Glu Arg Arg Val Leu Asp His Ala
195 200 205

Ala Val Arg Glu Leu Glu Thr Leu Ala Ala Asn Tyr Thr Ser Trp Ala
210 215 220

Asn Asp Leu His Ser Phe Ala Arg Glu His Arg Met Gly Gln Val Asn
225 230 235 240

Asn Leu Val Trp Ser Val His His His Glu Gly Leu Thr Phe Gln Gln
245 250 255

Ala Ala Asp Arg Val Ala Asp Leu Cys Asp Lys Glu Leu Ala Ala Tyr
260 265 270

Leu Glu Leu Arg Gln Thr Leu Pro Glu Leu Gly Ile Pro Leu Thr Gly
275 280 285

Ala Thr Gly Arg His Val Arg Phe Leu Glu Asp Met Met Trp Ser Met
290 295 300

Val Asp Trp Ser Ala Arg Ser Ala Arg Tyr Asp Val Val Pro Glu Ala
305 310 315 320

Ala

<210> SEQ ID NO 2
<211> LENGTH: 307
<212> TYPE: PRT
<213> ORGANISM: Streptomyces melanosporofaciens

<400> SEQUENCE: 2

Met Thr Thr Gly Leu Ser Thr Ala Gly Ala Gln Asp Ile Gly Arg Ser
1 5 10 15

Ser Val Arg Pro Tyr Leu Glu Glu Cys Thr Arg Arg Phe Gln Glu Met
20 25 30

Phe Asp Arg His Val Val Thr Arg Pro Thr Lys Val Glu Leu Thr Asp
35 40 45

Ala Glu Leu Arg Glu Val Ile Asp Asp Cys Asn Ala Ala Val Ala Pro
50 55 60

Leu Gly Lys Thr Val Ser Asp Glu Arg Trp Ile Ser Tyr Val Gly Val
65 70 75 80

Val Leu Trp Ser Gln Ser Pro Arg His Ile Lys Asp Met Glu Ala Phe
85 90 95

Lys Ala Val Cys Val Leu Asn Cys Val Thr Phe Val Trp Asp Asp Met
100 105 110

```
Asp Pro Ala Leu His Asp Phe Gly Leu Phe Leu Pro Gln Leu Arg Lys
        115                 120                 125

Ile Cys Glu Lys Tyr Tyr Gly Pro Glu Asp Ala Glu Val Ala Tyr Glu
    130                 135                 140

Ala Ala Arg Ala Phe Val Thr Ser Asp His Met Phe Arg Asp Ser Pro
145                 150                 155                 160

Ile Lys Ala Ala Leu Cys Thr Thr Ser Pro Glu Gln Tyr Phe Arg Phe
                165                 170                 175

Arg Val Thr Asp Ile Gly Val Asp Phe Trp Met Lys Met Ser Tyr Pro
            180                 185                 190

Ile Tyr Arg His Pro Glu Phe Thr Glu His Ala Lys Thr Ser Leu Ala
        195                 200                 205

Ala Arg Met Thr Thr Arg Gly Leu Thr Ile Val Asn Asp Phe Tyr Ser
    210                 215                 220

Tyr Asp Arg Glu Val Ser Leu Gly Gln Ile Thr Asn Cys Phe Arg Leu
225                 230                 235                 240

Cys Asp Val Ser Asp Glu Thr Ala Phe Lys Glu Phe Phe Gln Ala Arg
                245                 250                 255

Leu Asp Asp Met Ile Glu Asp Ile Glu Cys Ile Lys Ala Phe Asp Gln
            260                 265                 270

Leu Thr Gln Asp Val Phe Leu Asp Leu Ile Tyr Gly Asn Phe Val Trp
        275                 280                 285

Thr Thr Ser Asn Lys Arg Tyr Lys Thr Ala Val Asn Asp Val Asn Ser
    290                 295                 300

Arg Ile Gln
305
```

<210> SEQ ID NO 3
<211> LENGTH: 342
<212> TYPE: PRT
<213> ORGANISM: Amycolatopsis benzoatilytica

<400> SEQUENCE: 3

```
Met Pro Asn Val Glu Thr Gly Met Leu Pro Lys Gln Tyr Gln Arg Thr
1               5                   10                  15

Ser Thr Pro Asp Ile Asn Pro Ala Trp Gln Glu Ala Glu Asn Ala Phe
            20                  25                  30

Val Ser Tyr Ala Arg Lys Thr Gly Met Leu Thr Gly Gln Ala Asp Thr
        35                  40                  45

Thr Val Met Leu Ser Phe Gly Phe Gly Arg Phe Thr Gly Trp Ala Tyr
    50                  55                  60

Pro Asn Met Pro Thr Tyr Glu Leu Asn Leu Leu Thr Gln Trp His Tyr
65                  70                  75                  80

Trp Leu Thr Val Ala Asp Asp Val Ala Asp Ala Met Asn Ser Pro His
                85                  90                  95

Asp Ala His Arg Leu Arg Arg His Ile Leu Asp Ala Thr Ser Thr Arg
            100                 105                 110

Leu Pro Pro Glu Gln Gly Gly Pro Val Ala Ala Ser Phe His His Leu
        115                 120                 125

Trp Trp Arg Thr Ala Pro Ala Gln Ser Thr Glu Trp Gln Gln Arg Ala
    130                 135                 140

Arg Ala Ser Leu Ala Leu Tyr Leu Ser Ala Trp Ala Ser Gln Ser Asp
145                 150                 155                 160

Asn Arg Ser Arg Gly His Ile Val Thr Thr His Glu Tyr Ile Asp Ile
```

```
                165                 170                 175

Arg Arg Arg Ala Val Gly Leu Asp Ile Asn Thr Asp Val Leu Glu Ala
            180                 185                 190

Val His His Ile Thr Leu Pro Ala Pro Leu Phe Ala Thr Ser Ser Phe
        195                 200                 205

Arg Glu Leu Arg Asn Cys Phe Val Asp Ala Asn Ala Trp Phe Asn Asp
    210                 215                 220

Tyr Tyr Ser Tyr Glu Arg Glu Ala Thr Ser Gly Glu Asn His Asn Leu
225                 230                 235                 240

Ala Ile Val Leu Ala His Asn Gln Arg Met Pro Pro Gly Gln Ala Leu
                245                 250                 255

Asp Arg Val Leu Glu Met Ile Asn Thr Arg Leu Thr Thr Phe Leu Gln
            260                 265                 270

Ile Glu Arg Glu Leu Pro Asp Leu Val Ala Ala Leu Gly Tyr Pro Asp
        275                 280                 285

Glu Val Ala Thr Glu Val Leu Arg Tyr Thr Gln Ala Leu Arg Asp Tyr
    290                 295                 300

Thr Tyr Gly His Val Ala Trp Ser Ser Thr Ser Thr Arg Tyr Asn Asp
305                 310                 315                 320

Gln Gln Leu Arg Ala Thr Glu Trp Asn Arg Ala His His Ser Asn Asp
                325                 330                 335

His Pro Ala Arg Thr Glu
            340


<210> SEQ ID NO 4
<211> LENGTH: 374
<212> TYPE: PRT
<213> ORGANISM: Fusarium sporotrichioides

<400> SEQUENCE: 4

Met Glu Asn Phe Pro Thr Glu Tyr Phe Leu Asn Thr Thr Val Arg Leu
1               5                   10                  15

Leu Glu Tyr Ile Arg Tyr Arg Asp Ser Asn Tyr Thr Arg Glu Glu Arg
            20                  25                  30

Ile Glu Asn Leu His Tyr Ala Tyr Asn Lys Ala Ala His His Phe Ala
        35                  40                  45

Gln Pro Arg Gln Gln Gln Leu Leu Lys Val Asp Pro Lys Arg Leu Gln
    50                  55                  60

Ala Ser Leu Gln Thr Ile Val Gly Met Val Val Tyr Ser Trp Ala Lys
65                  70                  75                  80

Val Ser Lys Glu Cys Met Ala Asp Leu Ser Ile His Tyr Thr Tyr Thr
                85                  90                  95

Leu Val Leu Asp Asp Ser Lys Asp Asp Pro Tyr Pro Thr Met Val Asn
            100                 105                 110

Tyr Phe Asp Asp Leu Gln Ala Gly Arg Glu Gln Ala His Pro Trp Trp
        115                 120                 125

Ala Leu Val Asn Glu His Phe Pro Asn Val Leu Arg His Phe Gly Pro
    130                 135                 140

Phe Cys Ser Leu Asn Leu Ile Arg Ser Thr Leu Asp Phe Phe Glu Gly
145                 150                 155                 160

Cys Trp Ile Glu Gln Tyr Asn Phe Gly Gly Phe Pro Gly Ser His Asp
                165                 170                 175

Tyr Pro Gln Phe Leu Arg Arg Met Asn Gly Leu Gly His Cys Val Gly
            180                 185                 190
```

-continued

Ala Ser Leu Trp Pro Lys Glu Gln Phe Asn Glu Arg Ser Leu Phe Leu
195 200 205

Glu Ile Thr Ser Ala Ile Ala Gln Met Glu Asn Trp Met Val Trp Val
210 215 220

Asn Asp Leu Met Ser Phe Tyr Lys Glu Phe Asp Asp Glu Arg Asp Gln
225 230 235 240

Ile Ser Leu Val Lys Asn Tyr Val Val Ser Asp Glu Ile Ser Leu His
245 250 255

Glu Ala Leu Glu Lys Leu Thr Gln Asp Thr Leu His Ser Ser Lys Gln
260 265 270

Met Val Ala Val Phe Ser Asp Lys Asp Pro Gln Val Met Asp Thr Ile
275 280 285

Glu Cys Phe Met His Gly Tyr Val Thr Trp His Leu Cys Asp Arg Arg
290 295 300

Tyr Arg Leu Ser Glu Ile Tyr Glu Lys Val Lys Glu Glu Lys Thr Glu
305 310 315 320

Asp Ala Gln Lys Phe Cys Lys Phe Tyr Glu Gln Ala Ala Asn Val Gly
325 330 335

Ala Val Ser Pro Ser Glu Trp Ala Tyr Pro Pro Val Ala Gln Leu Ala
340 345 350

Asn Val Arg Ser Lys Asp Val Lys Glu Val Gln Lys Pro Phe Leu Ser
355 360 365

Ser Ile Glu Leu Val Glu
370

<210> SEQ ID NO 5
<211> LENGTH: 459
<212> TYPE: PRT
<213> ORGANISM: Streptomyces clavuligerus

<400> SEQUENCE: 5

Met Arg Gly Ala Gly Pro Gly Ser Val Arg Phe Ser Ser Leu Phe Ser
1 5 10 15

Gly Leu Gln Arg Ser Ser Ala Phe Phe Ser Ala Leu Arg Glu Ser Ser
20 25 30

Ala Phe Asp Val Arg His Arg Arg Gln Arg Val Ser His Glu Gln Arg
35 40 45

Val Pro Ser Val Ala Ala Arg Tyr Gly Gly Thr Ala Val His Ser Glu
50 55 60

Asp Ser Gly Pro Glu Asp Val Met Val Leu Arg Val Pro Glu Leu Gly
65 70 75 80

Arg Arg Leu Arg Pro Pro Arg Leu His Pro Ala Thr Pro Ala Val Val
85 90 95

Gly Gln Arg Val Pro Trp Leu Arg Asp Ala Leu Ala Asp Ile Glu Phe
100 105 110

Pro Gly Gly Thr Pro Glu Asp Phe Leu Arg Gln Asp Val His His Trp
115 120 125

Ser Val Tyr Cys Leu Pro Thr Ala Arg Ala Asp Arg Ile Ala Asp Leu
130 135 140

Ser Asn Ile His Glu Leu Ala Phe Ala Met Asp Asp Met Leu Glu Ser
145 150 155 160

Val His Asp Thr Asp Ala Asp Ala Asp Val His Thr Ala Ser Asp Leu
165 170 175

Asp Pro Ala Ser Gly Ser Ala Ser Asn Pro Gly Ser Gly Ser Gly Ser
180 185 190

-continued

```
Gly Phe Gly Ser Gly Phe Gly Arg Ala Ala Arg Arg Glu Arg Val Glu
        195                 200                 205

Pro Leu Ala Arg Ala Leu Glu Arg Ala Leu Ala Gly Leu Pro Pro Thr
    210                 215                 220

Gly Pro Val Pro Ser Tyr Leu Arg Ala Ala Asp Gly Cys Phe Arg Thr
225                 230                 235                 240

Leu Arg Glu Thr Gly Pro Ala Pro Trp Tyr Arg Arg Phe Gly Glu Ala
                245                 250                 255

Val Leu Ser Trp Phe His Gly Ala Val Lys Glu Ser Ser Met Met Ala
            260                 265                 270

Thr Gly Arg Leu Thr Gly Phe Glu Glu Thr Leu Asp Ser Arg Ile Asp
        275                 280                 285

Thr Ala Gly Gly Phe Phe Ile Ala Thr Ser Ile Glu Tyr Gly Leu Gly
    290                 295                 300

Ile Asp Leu Thr Asp Ala Ile Ala Ala Gly Pro Glu Leu Gly Glu Val
305                 310                 315                 320

Glu Arg Ala Ala Trp Val His Gly Val Leu Val Asn Asp Leu Phe Ser
                325                 330                 335

Tyr Arg Lys Glu His Phe Gly Glu Ala Gly Arg Ala Pro Asp Gly Arg
            340                 345                 350

Ala Pro Asp Gly Arg Ala Asn Thr Leu Arg Val Leu Ala Asp Glu Tyr
        355                 360                 365

Ala Cys Ser Leu Gln Glu Ala Val Asp Leu Leu Val Glu His Val Asp
    370                 375                 380

Ala Ala Glu Ala Arg Phe Leu Glu Leu Arg Ala Asp Val Leu Gly Ala
385                 390                 395                 400

Pro Leu Gly Ala Arg Pro Gly Val Arg Glu Tyr Leu Asp Ala Leu Glu
                405                 410                 415

Leu Val Leu Pro Gly Asn Ile Val Trp Ser Arg Thr Ser Arg Arg Tyr
            420                 425                 430

His Gly Thr Gly Cys Pro Trp Thr Gly Thr Ala Arg Thr Ala Met Ala
        435                 440                 445

Leu His Pro Asp Arg Thr Val Phe Thr Pro Trp
    450                 455
```

<210> SEQ ID NO 6
<211> LENGTH: 974
<212> TYPE: DNA
<213> ORGANISM: Streptomyces clavuligerus

<400> SEQUENCE: 6

```
atgcatatga ccattagcgt tccgcagctg gattgtccgc tgagccgtcc ggttcatccg     60

gaaggtgaac gtgcagatgc ctatgcagtt gaatggctgc gtggtgttgg tctgatggca    120

gatgaagcag atgcagcacc ggttctggca gttggtctgg gtcgtctggc agcatgttat    180

gttgatgaaa atgcaagctg ggataccctg gcatttatga ccattctgat ggcctggtat    240

gcagaatatg atgatcgtgc aattgatagt accggtgcca ttgatggtct gaccgatgca    300

gaagttgcag aactgcatcg tgcactgggt gaaattctgc gtgatcgtcc ggcacctgat    360

ccgagcgatc cggttcagcg tggtctggcg gatgtttggc gtaccctgaa tggtctggca    420

agcgattggg atcgtgcagc atttgttgat accaccctgc gttattttga agccaatcgt    480

tatgaacgtg tgaatattcg tcgtggtatt ccgcctaccc cgagcgcaca tattggtatg    540

cgtcgtcatg gtggtcatgt ttatggtatg tatattctgg gtgcagccgt taatggttat    600
```

-continued

```
cgtccggaac gtcgtgttct ggatcatgca gcagttcgtg aactggaaac cctggcagca    660

aattatacca gctgggcaaa tgatctgcat agctttgcac gtgaacatcg tatgggtcag    720

gttaataatc tggtttggag cgttcatcat catgaaggcc tgacctttca gcaggcagca    780

gatcgtgttg cagatctgtg tgataaagaa ctggcagcct atctggaact gcgtcagacc    840

ctgccggaac tgggcattcc gctgaccggt gcaacaggtc gtcatgttcg ttttctggaa    900

gatatgatgt ggtcaatggt tgattggagc gcacgtagtg cacgttatga tgttgttccg    960

gaagcagcat aagc                                                      974
```

```
<210> SEQ ID NO 7
<211> LENGTH: 321
<212> TYPE: PRT
<213> ORGANISM: Streptomyces clavuligerus

<400> SEQUENCE: 7

Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Leu Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Gly Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Met
    290                 295                 300
```

```
Val Asp Trp Ser Ala Arg Ser Ala Arg Tyr Asp Val Val Pro Glu Ala
305                 310                 315                 320

Ala


<210> SEQ ID NO 8
<211> LENGTH: 321
<212> TYPE: PRT
<213> ORGANISM: Artificial Sequence
<220> FEATURE:
<223> OTHER INFORMATION: Mutant of HpS

<400> SEQUENCE: 8

Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Tyr Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Gly Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Met
    290                 295                 300

Val Asp Trp Ser Ala Arg Ser Ala Arg Tyr Asp Val Val Pro Glu Ala
305                 310                 315                 320

Ala
```

<210> SEQ ID NO 9
<211> LENGTH: 321
<212> TYPE: PRT
<213> ORGANISM: Artificial Sequence
<220> FEATURE:
<223> OTHER INFORMATION: Mutant of HpS

<400> SEQUENCE: 9

```
Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Phe Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Gly Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Met
    290                 295                 300

Val Asp Trp Ser Ala Arg Ser Ala Arg Tyr Asp Val Val Pro Glu Ala
305                 310                 315                 320

Ala
```

<210> SEQ ID NO 10
<211> LENGTH: 321
<212> TYPE: PRT
<213> ORGANISM: Artificial Sequence
<220> FEATURE:
<223> OTHER INFORMATION: Mutant of HpS

<400> SEQUENCE: 10

Met Thr Ile Ser Val Pro Gln Leu Asp Cys Pro Leu Ser Arg Pro Val
1 5 10 15

His Pro Glu Gly Glu Arg Ala Asp Ala Tyr Ala Val Glu Trp Leu Arg
20 25 30

Gly Val Gly Leu Met Ala Asp Glu Ala Asp Ala Ala Pro Val Leu Ala
35 40 45

Val Gly Leu Gly Arg Leu Ala Ala Cys Tyr Val Asp Glu Asn Ala Ser
50 55 60

Trp Asp Thr Leu Ala Phe Met Thr Ile Leu Leu Ala Trp Tyr Ala Glu
65 70 75 80

Tyr Asp Asp Arg Ala Ile Asp Ser Thr Gly Ala Ile Asp Gly Leu Thr
85 90 95

Asp Ala Glu Val Ala Glu Leu His Arg Ala Leu Gly Glu Ile Leu Arg
100 105 110

Asp Arg Pro Ala Pro Asp Pro Ser Asp Pro Val Gln Arg Gly Leu Ala
115 120 125

Asp Val Trp Arg Thr Leu Asn Gly Leu Ala Ser Asp Trp Asp Arg Ala
130 135 140

Ala Phe Val Asp Thr Thr Leu Arg Tyr Phe Glu Ala Asn Arg Tyr Glu
145 150 155 160

Arg Val Asn Ile Arg Arg Gly Ile Pro Pro Thr Pro Ser Ala His Ile
165 170 175

Gly Met Arg Arg His Gly Gly His Val Tyr Gly Met Tyr Ile Leu Gly
180 185 190

Ala Ala Val Asn Gly Tyr Arg Pro Glu Arg Arg Val Leu Asp His Ala
195 200 205

Ala Val Arg Glu Leu Glu Thr Leu Ala Ala Asn Tyr Thr Ser Trp Ala
210 215 220

Asn Asp Leu His Ser Phe Ala Arg Glu His Arg Met Gly Gln Val Asn
225 230 235 240

Asn Leu Val Trp Ser Val His His His Glu Gly Leu Thr Phe Gln Gln
245 250 255

Ala Ala Asp Arg Val Ala Asp Leu Cys Asp Lys Glu Leu Ala Ala Tyr
260 265 270

Leu Glu Leu Arg Gln Thr Leu Pro Glu Leu Gly Ile Pro Leu Thr Gly
275 280 285

Ala Thr Gly Arg His Val Arg Phe Leu Glu Asp Met Met Trp Ser Met
290 295 300

Val Asp Trp Ser Ala Arg Ser Ala Arg Tyr Asp Val Val Pro Glu Ala
305 310 315 320

Ala

<210> SEQ ID NO 11
<211> LENGTH: 321
<212> TYPE: PRT
<213> ORGANISM: Artificial Sequence
<220> FEATURE:
<223> OTHER INFORMATION: Mutant of HpS

<400> SEQUENCE: 11

Met Thr Ile Ser Val Pro Gln Leu Asp Cys Pro Leu Ser Arg Pro Val
1 5 10 15

His Pro Glu Gly Glu Arg Ala Asp Ala Tyr Ala Val Glu Trp Leu Arg
20 25 30

```
Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Ala Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Met
    290                 295                 300

Val Asp Trp Ser Ala Arg Ser Ala Arg Tyr Asp Val Val Pro Glu Ala
305                 310                 315                 320

Ala


<210> SEQ ID NO 12
<211> LENGTH: 321
<212> TYPE: PRT
<213> ORGANISM: Artificial Sequence
<220> FEATURE:
<223> OTHER INFORMATION: Mutant of HpS

<400> SEQUENCE: 12

Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60
```

```
Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Phe Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Met
    290                 295                 300

Val Asp Trp Ser Ala Arg Ser Ala Arg Tyr Asp Val Val Pro Glu Ala
305                 310                 315                 320

Ala
```

<210> SEQ ID NO 13
<211> LENGTH: 321
<212> TYPE: PRT
<213> ORGANISM: Artificial Sequence
<220> FEATURE:
<223> OTHER INFORMATION: Mutant of HpS

<400> SEQUENCE: 13

```
Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
```

-continued

```
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Gly Gly Ala Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Met
    290                 295                 300

Val Asp Trp Ser Ala Arg Ser Ala Arg Tyr Asp Val Val Pro Glu Ala
305                 310                 315                 320

Ala


<210> SEQ ID NO 14
<211> LENGTH: 321
<212> TYPE: PRT
<213> ORGANISM: Artificial Sequence
<220> FEATURE:
<223> OTHER INFORMATION: Mutant of HpS

<400> SEQUENCE: 14

Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140
```

-continued

```
Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Gly Gly Phe Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Met
    290                 295                 300

Val Asp Trp Ser Ala Arg Ser Ala Arg Tyr Asp Val Val Pro Glu Ala
305                 310                 315                 320

Ala
```

<210> SEQ ID NO 15
<211> LENGTH: 321
<212> TYPE: PRT
<213> ORGANISM: Artificial Sequence
<220> FEATURE:
<223> OTHER INFORMATION: Mutant of HpS

<400> SEQUENCE: 15

```
Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175
```

```
Gly Met Arg Arg His Gly Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Ile Met Trp Ser Met
    290                 295                 300

Val Asp Trp Ser Ala Arg Ser Ala Arg Tyr Asp Val Val Pro Glu Ala
305                 310                 315                 320

Ala


<210> SEQ ID NO 16
<211> LENGTH: 321
<212> TYPE: PRT
<213> ORGANISM: Artificial Sequence
<220> FEATURE:
<223> OTHER INFORMATION: Mutant of HpS

<400> SEQUENCE: 16

Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Gly Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
```

-continued

```
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Ile
    290                 295                 300

Val Asp Trp Ser Ala Arg Ser Ala Arg Tyr Asp Val Val Pro Glu Ala
305                 310                 315                 320

Ala


<210> SEQ ID NO 17
<211> LENGTH: 321
<212> TYPE: PRT
<213> ORGANISM: Artificial Sequence
<220> FEATURE:
<223> OTHER INFORMATION: Mutant of HpS

<400> SEQUENCE: 17

Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Gly Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255
```

```
Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg His Val Arg Phe Leu Glu Asp Met Met Trp Ser Thr
    290                 295                 300

Val Asp Trp Ser Ala Arg Ser Ala Arg Tyr Asp Val Val Pro Glu Ala
305                 310                 315                 320

Ala


<210> SEQ ID NO 18
<211> LENGTH: 321
<212> TYPE: PRT
<213> ORGANISM: Artificial Sequence
<220> FEATURE:
<223> OTHER INFORMATION: Mutant of HpS

<400> SEQUENCE: 18

Met Thr Ile Ser Val Pro Gln Leu Asp Cys Pro Leu Ser Arg Pro Val
1               5                   10                  15

His Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu His Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala His Ile
                165                 170                 175

Gly Met Arg Arg His Gly Gly His Val Tyr Gly Met Tyr Ile Leu Gly
            180                 185                 190

Ala Ala Val Asn Gly Tyr Arg Pro Glu Arg Arg Val Leu Asp His Ala
        195                 200                 205

Ala Val Arg Glu Leu Glu Thr Leu Ala Ala Asn Tyr Thr Ser Trp Ala
    210                 215                 220

Asn Asp Leu His Ser Phe Ala Arg Glu His Arg Met Gly Gln Val Asn
225                 230                 235                 240

Asn Leu Val Trp Ser Val His His His Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285
```

```
Ala Thr Gly Arg His Val Arg Phe Leu Glu Asp Met Met Trp Ser Cys
    290                 295                 300

Val Asp Trp Ser Ala Arg Ser Ala Arg Tyr Asp Val Val Pro Glu Ala
305                 310                 315                 320

Ala


<210> SEQ ID NO 19
<211> LENGTH: 5
<212> TYPE: PRT
<213> ORGANISM: Streptomyces clavuligerus
<220> FEATURE:
<221> NAME/KEY: misc_feature
<222> LOCATION: (3)..(4)
<223> OTHER INFORMATION: Xaa can be any naturally occurring amino acid

<400> SEQUENCE: 19

Asp Asp Xaa Xaa Asp
1               5


<210> SEQ ID NO 20
<211> LENGTH: 4
<212> TYPE: PRT
<213> ORGANISM: Streptomyces clavuligerus

<400> SEQUENCE: 20

Asp Asp Met Asp
1


<210> SEQ ID NO 21
<211> LENGTH: 6
<212> TYPE: PRT
<213> ORGANISM: Streptomyces clavuligerus

<400> SEQUENCE: 21

Asp Asp Arg Ala Ile Asp
1               5


<210> SEQ ID NO 22
<211> LENGTH: 9
<212> TYPE: PRT
<213> ORGANISM: Streptomyces clavuligerus

<400> SEQUENCE: 22

Asn Asp Phe Tyr Ser Tyr Asp Arg Glu
1               5


<210> SEQ ID NO 23
<211> LENGTH: 9
<212> TYPE: PRT
<213> ORGANISM: Streptomyces clavuligerus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 23

Asn Asp Leu Xaa Ser Phe Ala Arg Glu
1               5


<210> SEQ ID NO 24
<211> LENGTH: 8
<212> TYPE: PRT
<213> ORGANISM: Streptomyces clavuligerus

<400> SEQUENCE: 24
```

-continued

Trp Thr Thr Ser Asn Lys Arg Tyr
1 5

<210> SEQ ID NO 25
<211> LENGTH: 8
<212> TYPE: PRT
<213> ORGANISM: Streptomyces clavuligerus

<400> SEQUENCE: 25

Trp Ser Ala Arg Ser Ala Arg Tyr
1 5

<210> SEQ ID NO 26
<211> LENGTH: 317
<212> TYPE: PRT
<213> ORGANISM: Artificial Sequence
<220> FEATURE:
<223> OTHER INFORMATION: HpS
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (247)..(249)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid

<400> SEQUENCE: 26

Met Thr Ile Ser Val Pro Gln Leu Asp Cys Pro Leu Ser Arg Pro Val
1 5 10 15

Xaa Pro Glu Gly Glu Arg Ala Asp Ala Tyr Ala Val Glu Trp Leu Arg
20 25 30

Gly Val Gly Leu Met Ala Asp Glu Ala Asp Ala Ala Pro Val Leu Ala
35 40 45

Val Gly Leu Gly Arg Leu Ala Ala Cys Tyr Val Asp Glu Asn Ala Ser
50 55 60

Trp Asp Thr Leu Ala Phe Met Thr Ile Leu Met Ala Trp Tyr Ala Glu
65 70 75 80

-continued

```
Tyr Asp Asp Arg Ala Ile Asp Ser Thr Gly Ala Ile Asp Gly Leu Thr
                85                  90                  95

Asp Ala Glu Val Ala Glu Leu Xaa Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala Xaa Ile
                165                 170                 175

Gly Met Arg Arg Xaa Gly Gly Xaa Val Tyr Gly Met Tyr Ile Leu Gly
            180                 185                 190

Ala Ala Val Asn Gly Tyr Arg Pro Glu Arg Arg Val Leu Asp Xaa Ala
        195                 200                 205

Ala Val Arg Glu Leu Glu Thr Leu Ala Ala Asn Tyr Thr Ser Trp Ala
    210                 215                 220

Asn Asp Leu Xaa Ser Phe Ala Arg Glu Xaa Arg Met Gly Gln Val Asn
225                 230                 235                 240

Asn Leu Val Trp Ser Val Xaa Xaa Xaa Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg Xaa Val Arg Phe Leu Glu Asp Met Met Trp Ser Met
    290                 295                 300

Val Asp Trp Ser Ala Arg Ser Ala Arg Tyr Asp Val Val
305                 310                 315
```

<210> SEQ ID NO 27
<211> LENGTH: 324
<212> TYPE: PRT
<213> ORGANISM: Artificial Sequence
<220> FEATURE:
<223> OTHER INFORMATION: HpS
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (228)..(228)

-continued

<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (247)..(249)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (322)..(324)
<223> OTHER INFORMATION: Xaa can be any naturally occurring amino acid

<400> SEQUENCE: 27

```
Met Thr Ile Ser Val Pro Gln Leu Asp Cys Pro Leu Ser Arg Pro Val
1               5                   10                  15

Xaa Pro Glu Gly Glu Arg Ala Asp Ala Tyr Ala Val Glu Trp Leu Arg
            20                  25                  30

Gly Val Gly Leu Met Ala Asp Glu Ala Asp Ala Ala Pro Val Leu Ala
        35                  40                  45

Val Gly Leu Gly Arg Leu Ala Ala Cys Tyr Val Asp Glu Asn Ala Ser
    50                  55                  60

Trp Asp Thr Leu Ala Phe Met Thr Ile Leu Met Ala Trp Tyr Ala Glu
65                  70                  75                  80

Tyr Asp Asp Arg Ala Ile Asp Ser Thr Gly Ala Ile Asp Gly Leu Thr
                85                  90                  95

Asp Ala Glu Val Ala Glu Leu Xaa Arg Ala Leu Gly Glu Ile Leu Arg
            100                 105                 110

Asp Arg Pro Ala Pro Asp Pro Ser Asp Pro Val Gln Arg Gly Leu Ala
        115                 120                 125

Asp Val Trp Arg Thr Leu Asn Gly Leu Ala Ser Asp Trp Asp Arg Ala
    130                 135                 140

Ala Phe Val Asp Thr Thr Leu Arg Tyr Phe Glu Ala Asn Arg Tyr Glu
145                 150                 155                 160

Arg Val Asn Ile Arg Arg Gly Ile Pro Pro Thr Pro Ser Ala Xaa Ile
                165                 170                 175

Gly Met Arg Arg Xaa Gly Gly Xaa Val Tyr Gly Met Tyr Ile Leu Gly
            180                 185                 190

Ala Ala Val Asn Gly Tyr Arg Pro Glu Arg Arg Val Leu Asp Xaa Ala
        195                 200                 205

Ala Val Arg Glu Leu Glu Thr Leu Ala Ala Asn Tyr Thr Ser Trp Ala
    210                 215                 220

Asn Asp Leu Xaa Ser Phe Ala Arg Glu Xaa Arg Met Gly Gln Val Asn
225                 230                 235                 240

Asn Leu Val Trp Ser Val Xaa Xaa Xaa Glu Gly Leu Thr Phe Gln Gln
                245                 250                 255

Ala Ala Asp Arg Val Ala Asp Leu Cys Asp Lys Glu Leu Ala Ala Tyr
            260                 265                 270

Leu Glu Leu Arg Gln Thr Leu Pro Glu Leu Gly Ile Pro Leu Thr Gly
        275                 280                 285

Ala Thr Gly Arg Xaa Val Arg Phe Leu Glu Asp Met Met Trp Ser Met
    290                 295                 300

Val Asp Trp Ser Ala Arg Ser Ala Arg Tyr Asp Val Val Pro Glu Ala
305                 310                 315                 320
```

```
Ala Xaa Xaa Xaa


<210> SEQ ID NO 28
<211> LENGTH: 346
<212> TYPE: PRT
<213> ORGANISM: Artificial Sequence
<220> FEATURE:
<223> OTHER INFORMATION: ABS

<400> SEQUENCE: 28

Met Thr Gly Gly Val Pro Asn Val Glu Thr Gly Met Leu Pro Lys Gln
1               5                   10                  15

Tyr Gln Arg Thr Ser Thr Pro Asp Ile Asn Pro Ala Trp Gln Glu Ala
            20                  25                  30

Glu Asn Ala Phe Val Ser Tyr Ala Arg Lys Thr Gly Met Leu Thr Gly
        35                  40                  45

Gln Ala Asp Thr Thr Val Met Leu Ser Phe Gly Phe Gly Arg Phe Thr
    50                  55                  60

Gly Trp Ala Tyr Pro Asn Met Pro Thr Tyr Glu Leu Asn Leu Leu Thr
65                  70                  75                  80

Gln Trp His Tyr Trp Leu Thr Val Ala Asp Asp Val Ala Asp Ala Met
                85                  90                  95

Asn Ser Pro His Asp Ala His Arg Leu Arg Arg His Ile Leu Asp Ala
            100                 105                 110

Thr Ser Thr Arg Leu Pro Pro Glu Gln Gly Gly Pro Val Ala Ala Ser
        115                 120                 125

Phe His His Leu Trp Trp Arg Thr Ala Pro Ala Gln Ser Thr Glu Trp
    130                 135                 140

Gln Gln Arg Ala Arg Ala Ser Leu Ala Leu Tyr Leu Ser Ala Trp Ala
145                 150                 155                 160

Ser Gln Ser Asp Asn Arg Ser Arg Gly His Ile Val Thr Thr His Glu
                165                 170                 175

Tyr Ile Asp Ile Arg Arg Arg Ala Val Gly Leu Asp Ile Asn Thr Asp
            180                 185                 190

Val Leu Glu Ala Val His His Ile Thr Leu Pro Ala Pro Leu Phe Ala
        195                 200                 205

Thr Ser Ser Phe Arg Glu Leu Arg Asn Cys Phe Val Asp Ala Asn Ala
    210                 215                 220

Trp Phe Asn Asp Tyr Tyr Ser Tyr Glu Arg Glu Ala Thr Ser Gly Glu
225                 230                 235                 240

Asn His Asn Leu Ala Ile Val Leu Ala His Asn Gln Arg Met Pro Pro
                245                 250                 255

Gly Gln Ala Leu Asp Arg Val Leu Glu Met Ile Asn Thr Arg Leu Thr
            260                 265                 270

Thr Phe Leu Gln Ile Glu Arg Glu Leu Pro Asp Leu Val Ala Ala Leu
        275                 280                 285

Gly Tyr Pro Asp Glu Val Ala Thr Glu Val Leu Arg Tyr Thr Gln Ala
    290                 295                 300

Leu Arg Asp Tyr Thr Tyr Gly His Val Ala Trp Ser Ser Thr Ser Thr
305                 310                 315                 320

Arg Tyr Asn Asp Gln Gln Leu Arg Ala Thr Glu Trp Asn Arg Ala His
                325                 330                 335

His Ser Asn Asp His Pro Ala Arg Thr Glu
            340                 345
```

MODIFIED TERPENE SYNTHASES AND THEIR USE FOR PRODUCTION OF PSEUDOPTEROSIN INTERMEDIATES AND/OR PSEUDOPTEROSINS

CROSS REFERENCE TO RELATED APPLICATIONS

This application is a National Stage Application of International Application Number PCT/EP2021/068363, filed Jul. 2, 2021; which claims priority to European Patent Application No. 20183732.5, filed Jul. 2, 2020, both of which are incorporated herein by reference in their entirety.

SEQUENCE LISTING

The Sequence Listing for this application is labeled "SeqList19Jan26-ST25.txt", which was created on Jan. 19, 2026 and is 63,922 bytes. The entire content is incorporated herein by reference in its entirety.

FIELD OF THE INVENTION

The present invention pertains to novel modified terpene synthases and their use for a preparation method for pseudopterosin intermediates and/or pseudopterosins. The method is based on the use of a modified terpene synthase comprising at least one modified amino acid residue, which enables a terpene synthase-catalyzed increased production of pseudopterosin intermediates and/or pseudopterosins from Geranylgeranyl pyrophosphate as starting material. The new modified terpene synthases of this invention allow the production of pseudopterosin intermediates, such as Isoelisabethatriene A, Isoelisabethatriene B, Erogorgiaene, or Seco-Pseudopterosin and/or the production of pseudopterosins, such as Pseudopterosin A, in a cost-efficient, economical, and sustainable manner. Also provided are nucleic acids, encoding for the modified terpene synthases of this invention, as well as expression vectors capable of expressing said nucleic acids and host cells comprising the same.

DESCRIPTION

Global population increase twinned with unsustainable lifestyles drive climate change and the evolution of new, contractible diseases. For the latter, new anti-infective and anti-inflammatory drugs have to be developed as a first-line treatment response. Natural products are a treasure trove for new drug leads, and with over 50,000 characterized compounds, terpenes represent the structurally most diverse natural product family. The diterpenoid subfamily encompasses a diverse range of bioactivities including antioxidant, anti-inflammatory, antiviral, antimalarial, antibiotic and antitumor agents, such as the clinically important Taxol. Diterpenes found in plants, fungi and prokaryotes feature a unique, highly functionalized, structurally complex macrocyclic core. This macrocyclic scaffold is formed by cyclisation of the universal aliphatic diterpene precursor geranylgeranyl diphosphate (GGPP), a reaction catalysed by the enigmatic family of diterpene synthases.

As diterpene-type natural products predominantly represent secondary metabolites, only minor amounts can routinely be obtained from their respective natural source, often demanding elaborate purification strategies. Moreover, their structural complexity demands uneconomical, multi-step total synthesis approaches. Therefore, commercialization of diterpenoid drug leads is hampered by lack of sustainable and/or cost-efficient supply routes.

One pharmaceutically highly promising diterpene derivative is the class of Pseudopterosins. The Pseudopterosins are amphilectane type diterpene glycosides with up to date 31 members, which were originally isolated from the Caribbean gorgonian coral *Antillogorgia elisabethae*. Pseudopterosins feature potent anti-inflammatory, wound healing and analgesic activities, which significantly exceed those of their non-steroidal, synthetic counterpart indomethacin. The superior anti-inflammatory action and reduced side effects are due to a new pharmacological mode of action. Notably, the advanced biosynthetic pseudopterosin precursor erogorgiaene exhibits significant antibiotic activity, particularly against *Mycobacterium tuberculosis*, the causative agent of drug-resistant tuberculosis.

In addition to Pseudopterosins, a related second class of diterpene glycoside, so-called seco-Pseudopterosins, has been identified from *A. elisabethae*. The seco-Pseudopterosins belong to the class of serrulatane type diterpene glycosides and also show anti-inflammatory and analgesic activities.

Commercially, pseudopterosins are applied as natural, marine anti-irritants in diverse skincare products associated with a multi-billion Euro market value. However, the ever-expanding Pseudopterosins' demand is currently exclusively met by harvesting and extracting its natural source. This practice is neither scalable nor sustainable, as it leads to extensive destruction of sensitive coral reef ecosystems, which are under increasing pressure from climate change effects. As efficient total chemical syntheses are not available, this inherent supply issue has also precluded the development of clinically useful compounds from this family of natural products. While pseudopterosins have progressed to phase II clinical trials as a topical anti-inflammatory agent, further clinical development has been discontinued due to insufficient supply. Hence, there is an urgent need for providing alternative, sustainable and coral-independent productions routes for pseudopterosins and/or pseudopterosin intermediates, for example using an engineered microbial chassis (e.g. *Escherichia coli*).

Previous studies reported methods for Pseudopterosin isolation and/or synthesis. WO03030820A2 describes methods for obtaining at least one pseudopterosin compound by obtaining, isolating, purifying or preparing the pseudopterosin compound from an organism belonging to the genus *Symbiodinium*.

Newton et al. (2015) disclose a method for Pseudopterosin synthesis from a chiral cross-conjugated hydrocarbon through a series of cycloadditions.[1]

Davies et al. (2005) describes a method, where a combined C—H activation/Cope rearrangement catalyzed by dirhodium tetraprolinate is used to enable a direct synthesis of the pseudopterosin precursor (+)-erogorgiaene through a kinetic enantio-differentiating step.[2]

However, none of the previous attempts aiming at obtaining and/or synthesizing various pseudopterosins and/or their bioactive intermediates allowed a cost-efficient, economical, sustainable, and scalable supply of pseudopterosins and/or their intermediates.

Due to the continuing need for a biotechnological production method of pseudopterosins and their intermediates, the present invention seeks to provide a novel biotechnological production method of pseudopterosins and their intermediates that is cost-efficient, economical, scalable and sustainable.

The inventors were able to overcome the above problem by mutating certain amino acid residues of terpene synthases. Based on this solution, the invention provides a sustainable biotechnological and coral-independent route for production of biosynthetic pseudopterosin precursors en-route to a consolidated, scalable, and sustainable production of Pseudopterosin-type bioactive compounds. The mechanisms enabled by this invention will significantly contribute to coral reef protection and provide clinical access to new antibiotic and anti-inflammatory drugs. These compounds can be applied in first line-treatments to control contagion agents and diseases associated with excessive inflammatory response during infective epidemics (i.e. COVID-19). Moreover, these pseudopterosin type compounds can be applied in chronic inflammatory diseases.

BRIEF DESCRIPTION OF THE INVENTION

Generally, and by way of brief description, the main aspects of the present invention can be described as follows:

In a first aspect, the invention provides enzymes capable of producing pseudopterosins and their intermediates.

In a second aspect, the invention pertains to a method of preparing pseudopterosins and their intermediates using the enzymes of this invention.

In a third aspect, the invention pertains to a sustainable and scalable biotechnological production method for pseudopterosins and their intermediates.

In a fourth aspect, the invention pertains to nucleic acids, encoding for the enzymes of this invention, as well as expression vectors capable of expressing said nucleic acids and host cells comprising the same.

DETAILED DESCRIPTION OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

In a first aspect, the invention pertains to a modified terpene synthase comprising at least one modified amino acid residue as compared to the amino acid sequence corresponding to an unmodified wild type terpene synthase according to any one of SEQ ID NOs: 1 to 5, wherein said at least one modified amino acid residue is located in an α-helix structure being part of or close to an active site pocket of the terpene synthase, and wherein said at least one modified amino acid residue is an amino acid with a hydrophobic side chain, such as alanine, valine, isoleucine, leucine, methionine, phenylalanine, tyrosine, or tryptophan, and/or an amino acid with a polar uncharged side chain, such as threonine, cysteine, asparagine, glutamine, or serine.

In one preferred embodiment, the present invention pertains to a modified terpene synthase comprising at least one modified amino acid residue as compared to an amino acid sequence of an unmodified wild type terpene synthase, wherein said at least one modified amino acid residue is a substitution of a wild type amino acid residue (or of several wild type amino acid residues) for an amino acid residue (or several amino acid residues, each) having a hydrophobic side chain, such as alanine, valine, isoleucine, leucine, methionine, phenylalanine, tyrosine, or tryptophan, and/or for an amino acid residue (or several amino acid residues, each) having a polar uncharged side chain such as threonine, cysteine, asparagine, glutamine, or serine.

The term "modified terpene synthase" as used herein, preferably refers to a terpene synthase wherein such modified terpene synthase catalyzes the production of at least one pseudopterosin intermediate, such as Elisabethatriene, Isoelisabethatriene A, Isoelisabethatriene B, Erogorgiaene, or Seco-Pseudopterosin, and/or the production of at least one pseudopterosin such as Pseudopterosin A, from Geranylgeranyl pyrophosphate (GGPP) in a host cell in an amount that is greater than the amount of said pseudopterosin intermediate and/or of the same pseudopterosin produced from GGPP by the unmodified wild type terpene synthase in the same host cell and under the same conditions; and/or wherein the modified terpene synthase catalyzes the production of at least one side product, such as Hydropyrene (HP) or Hydropyrenol (HP-ol), from GGPP in a host cell in an amount that is smaller than the amount of said side product, such as HP or HP-ol, produced from GGPP by the unmodified wild type terpene synthase in the same host cell and under the same conditions.

As used in the context of this invention, the term terpene synthase shall refer to any kind of terpene synthase, such as Hydropyrene synthase (HpS), class I terpene synthase CotB2 from *Streptomyces melanosporofaciens*, the Diterpene Synthase from *Amycolatopsis benzoatilytica* (ABS), a Trichodiene Synthase, a Clavulatriene Synthase, the terpene synthase from *Hyoscyamus muticus* Vestipiradiene synthase, citrus valencene synthase (CVS), (+)-Bornyl diphosphate synthase (BDS), *Vitis vinifera* valencene synthase (Vv CVS), bergamotene synthase (BS), *Nicotiana tabacum* 5-epi-aristolochene synthase (TEAS), germacrene A, amorpha-4,11-diene synthase (ADS), *Hyoscyamus muticus* premnaspirodiene synthase, and preferably to a diterpene synthase selected from HpS, CotB2, ABS, Trichodiene Synthase, and Clavulatriene Synthase.

To overcome the above challenges, the inventors identified bacterial terpene synthases, such as Hydropyrene synthase (HpS) from *Streptomyces clavuligerus*, that produce Pseudopterosin precursors. In nature, the bacterial terpene synthase HpS generates hydropyrene (HP) (around 52%) and hydropyrenol (HPol) (around 26%) as its main geranylgeranyl diphosphate (GGPP) cyclization products, along with two minor products, namely the elisabethatriene isomers isoelisabethatriene (IE) A (around 12%) and isoelisabethatriene (IE) B (around 9%), respectively. In an attempt to enhance IE A and IE B production, the inventors found that modifying said terpene synthases by introducing at least one modified amino acid residue increases the production of pseudopterosin intermediates, such as Elisabethatriene, Isoelisabethatriene A, Isoelisabethatriene B, Erogorgiaene, and/or Seco-Pseudopterosin, and/or the production of pseudopterosins, such as Pseudopterosin A, from Geranylgeranyl pyrophosphate (GGPP) as starting material and a concurrent reduced production of Hydropyrene or Hydropyrenol. Interestingly, IE A and IE B differ only in the position of unsaturation within their bicyclic carbon skeleton with reference to the confirmed pseudopterosin precursor, elisabethatriene (FIG. 1). Therefore, these compounds may replace elisabethatriene in a designed biotechnological pseudopterosin synthesis cascade (FIG. 2).

The inventors were able to overcome the above problem by mutating amino acid residues of terpene synthases involved in stabilizing intermediates from GGPP in the reaction pathway favoring the generation of Hydropyrene derivatives as product. To pursue a reaction pathway towards Hydropyrene derivatives, a key carbocation intermediate C1 needs to be stabilized. Thus, preventing said carbocation intermediate C1 stabilization in the reaction from GGPP catalyzed by terpene synthases, such as HpS, prevents generation of Hydropyrene derivatives as product. The inventors found that the mutations of this invention are destabilizing the key C1 intermediate and, therefore, show a product shift towards pseudopterosin intermediates, such as IE A and B, as the dominant GGPP cyclisation products.

Terpene synthases comprise an α-helix and/or α-barrel structure being part of or close to an active site pocket of said terpene synthase. Mutating at least one amino acid residue located in an α-helix structure being part of or close to an active site pocket in said terpene synthase enables the generation of a large amount of pseudopterosin intermediates, such as IE A or IE B, instead of HP and/or HPol. In this invention, residues were chosen for a site directed mutagenesis approach to shift the product spectrum towards pseudopterosin intermediates, which are potentially carbocation shaping, hydrophobic or stereochemical demanding within the terpene synthase active site.

In a preferred embodiment, the modified terpene synthase has at least 75% sequence identity to the unmodified wild type terpene synthase according to any one of SEQ ID NOs: 1 to 5, preferably wherein the modified terpene synthase has at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the unmodified wild type terpene synthase according to any one of SEQ ID NOs: 1 to 5.

A particularly preferred embodiment relates to a modified terpene synthase, wherein the modified terpene synthase catalyzes the production of at least one pseudopterosin intermediate, such as Elisabethatriene, Isoelisabethatriene A, Isoelisabethatriene B, Erogorgiaene, or Seco-Pseudopterosin, and/or the production of at least one pseudopterosin, such as Pseudopterosin A, from Geranylgeranyl pyrophosphate (GGPP) in a host cell in an amount that is greater than the amount of said pseudopterosin intermediate and/or the same pseudopterosin produced from GGPP by the unmodified wild type terpene synthase having the amino acid sequence according to any one of SEQ ID NOs: 1 to 5 in the same host cell and under the same conditions, and/or wherein the modified terpene synthase catalyzes the production of at least one side product, such as Hydropyrene (HP) or Hydropyrenol (HP-ol), from GGPP in a host cell in an amount that is smaller than the amount of said side product, such as HP or HP-ol, produced from GGPP by the unmodified wild type terpene synthase having the amino acid sequence according to any one of SEQ ID NOs: 1 to 5 in the same host cell and under the same conditions.

The term "catalyzes" as used herein shall refer to enhancing the production of an immediate product of a reaction, and shall also refer to enhancing the production of subsequent products of said immediate product and the final product of the biocatalytic cascade. Thus, the term catalyzes refers to the production of any immediate product catalysed by a terpene synthase, but also to any product generated from this immediate product. For example, the term catalyzes shall refer to the production of a pseudopterosin intermediate, such as Elisabethatriene, Isoelisabethatriene A, Isoelisabethatriene B, Erogorgiaene, or Seco-Pseudopterosin, and shall also refer to the production of at least one pseudopterosin, such as Pseudopterosin A, further derived from said pseudopterosin intermediate, such as Elisabethatriene, Isoelisabethatriene A, Isoelisabethatriene B, Erogorgiaene, or Seco-Pseudopterosin. In the context of this invention, the host cell is preferably a bacterial cell or a yeast cell. However, the present invention is not limited thereto.

Additionally preferred is a modified terpene synthase, wherein the amount of the at least one pseudopterosin intermediate and/or the least one pseudopterosin produced from GGPP by the modified terpene synthase is increased by 0 to 100 percentage points, preferably by 10 to 80 percentage points, more preferably by 20 to 60 percentage points, even more preferably by 30 to 40 percentage points, and most preferably by around 32 percentage points compared to the amount of the at least one pseudopterosin intermediate and/or the least one pseudopterosin produced from GGPP by the unmodified wild type terpene synthase having an amino acid sequence according to any one of SEQ ID NOs: 1 to 5, and/or wherein the amount of said at least one side product, such as HP or HP-ol, produced from GGPP by the modified terpene synthase is decreased by 0 to 100 percentage points, preferably by 5 to 80 percentage points, more preferably by 10 to 40 percentage points, such as by around 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 percentage points, even more preferably by 20 to 30 percentage points, and most preferably by around 26, 21, or 20 percentage points compared to the amount of said at least one side product, such as HP or HP-ol, produced from GGPP by the unmodified wild type terpene synthase having an amino acid sequence according to any one of SEQ ID NOs: 1 to 5.

As used in the context of this invention, "in an amount that is greater than" shall refer to an enhancement of at least 1 percentage points, preferably at least 10 percentage points, more preferably at least 20 percentage points, even more preferably at least 30 percentage points, and most preferably around 32 percentage points. The term "in an amount that is smaller than" shall refer to a reduction of at least 1 percentage points, preferably at least 5 percentage points, more preferably at least 10 percentage points, and most preferably at least 20 percentage points.

Interestingly, the inventors identified the mutation M75F in HpS, which showed a product range of 20% IE A (1.6-fold increase), 41% IE B (4.5-fold increase), 34% Hydropyrene (1.5-fold decrease) and 5% Hydropyrenol (5.2-fold decrease). HpS mutant M71Y showed 25% IE A (2.1-fold increase), 16% IE B (1.8-fold increase), 35% Hydropyrene (1.5-fold decrease) and 24% Hydropyrenol (1.1-fold decrease). Mutant M75L showed a product spectrum of 44% IE A (3.7-fold increase), 24% IE B (2.7-fold increase), 26% Hydropyrene (2.0-fold decrease) and 6% Hydropyrenol (4.3-fold decrease).

Thus, in an exemplary embodiment of this invention a modified terpene synthase is particularly preferred, wherein the modified terpene synthase comprises e.g. the modified amino acid residue M75F in the amino acid sequence of the unmodified wild type HpS according to SEQ ID NO: 1, or wherein said at least one modified amino acid residue is a substitution of a wild type amino acid residue located at an equivalent position of an unmodified wild type terpene synthase according to any one of SEQ ID NOs: 2 to 5. In this exemplary embodiment of this invention, a modified terpene synthase is provided, wherein the amount of at least one pseudopterosin intermediate, IE A, produced from GGPP by the modified terpene synthase is characterized by a 1.6-fold increase compared to the unmodified wild type terpene synthase. This exemplary embodiment also pertains to a modified terpene synthase, wherein the amount of the at least one pseudopterosin intermediate, IE B, produced from GGPP by the modified terpene synthase is characterized by a 4.5-fold increase compared to an unmodified wild type terpene synthase. Further preferred is the exemplary modified terpene synthase, wherein the amount of said at least one side product, HP, produced from GGPP by the modified terpene synthase is characterized by a 1.5-fold decrease compared to the unmodified wild type terpene synthase. Also preferred is this modified terpene synthase, wherein the amount of said at least one side product, such as HP-ol, produced from GGPP by the modified terpene synthase is characterized by a 5.2-fold decrease compared to the unmodified wild type terpene synthase.

In another exemplary embodiment of this invention, a modified terpene synthase is particularly preferred, wherein the modified terpene synthase comprises e.g. the modified amino acid residue M71Y in the amino acid sequence of the unmodified wild type HpS according to SEQ ID NO: 1, or wherein said at least one modified amino acid residue is a substitution of a wild type amino acid residue located at an equivalent position of an unmodified wild type terpene synthase according to any one of SEQ ID NOs: 2 to 5. In this exemplary embodiment of this invention, a modified terpene synthase is provided, wherein the amount of at least one pseudopterosin intermediate, IE A, produced from GGPP by the modified terpene synthase is characterized by a 2.1-fold increase compared to the unmodified wild type terpene synthase. This exemplary embodiment also pertains to a modified terpene synthase, wherein the amount of the at least one pseudopterosin intermediate, IE B, produced from GGPP by the modified terpene synthase is characterized by a 1.8-fold increase compared to an unmodified wild type terpene synthase. Further preferred is this modified terpene synthase, wherein the amount of said at least one side product, HP, produced from GGPP by the modified terpene synthase is characterized by a 1.5-fold decrease compared to the unmodified wild type terpene synthase. Also preferred is this modified terpene synthase, wherein the amount of said at least one side product, such as HP-ol, produced from GGPP by the modified terpene synthase is characterized by a 1.1-fold decrease compared to the unmodified wild type terpene synthase.

Yet another exemplary embodiment of this invention pertains to a modified terpene synthase, wherein the modified terpene synthase comprises e.g. the modified amino acid residue M75L in the amino acid sequence of the unmodified wild type HpS according to SEQ ID NO: 1, or wherein said at least one modified amino acid residue is a substitution of a wild type amino acid residue located at an equivalent position of an unmodified wild type terpene synthase according to any one of SEQ ID NOs: 2 to 5. In this exemplary embodiment of this invention, a modified terpene synthase is provided, wherein the amount of at least one pseudopterosin intermediate, IE A, produced from GGPP by the modified terpene synthase is characterized by a 3.7-fold increase compared to the unmodified wild type terpene synthase. This exemplary embodiment also pertains to a modified terpene synthase, wherein the amount of the at least one pseudopterosin intermediate, IE B, produced from GGPP by the modified terpene synthase is characterized by a 2.7-fold increase compared to an unmodified wild type terpene synthase. Further preferred is this modified terpene synthase, wherein the amount of said at least one side product, HP, produced from GGPP by the modified terpene synthase is characterized by a 2.0-fold decrease compared to the unmodified wild type terpene synthase. Also preferred is this modified terpene synthase, wherein the amount of said at least one side product, such as HP-ol, produced from GGPP by the modified terpene synthase is characterized by a 4.3-fold decrease compared to the unmodified wild type terpene synthase.

Yet another particularly preferred embodiment relates to a modified terpene synthase, wherein the number of said at least one modified amino acid residue in the modified terpene synthase compared to the unmodified terpene synthase according to any one of SEQ ID NOs: 1 to 5 is at least 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acid residues.

In all aspects and embodiments of the present invention it may be preferred that the terpene synthase is a Hydropyrene synthase (HpS), such as a bacterial diterpene synthase from *Streptomyces clavuligerus* comprising the amino acid sequence according to SEQ ID NO: 1, a class I terpene synthase, such as CotB2 from *Streptomyces melanosporofaciens* comprising the amino acid sequence according to SEQ ID NO: 2, a diterpene synthase, such as the diterpene synthase from *Amycolatopsis benzoatilytica* (ABS) comprising the amino acid sequence according to SEQ ID NO: 3, a Trichodiene synthase, such as a Trichodiene synthase from *Fusarium sporotrichioides* comprising the amino acid sequence according to SEQ ID NO: 4, or a Clavulatriene synthase, such as Clavulatriene synthase from *Streptomyces clavuligerus*, comprising the amino acid sequence according to SEQ ID NO: 5.

As a reference, the designations of the wild type, unmodified terpene synthases of this invention are referring to their respective entries in the UniProt database ("www.uniprot.org/") and/or NCBI GenBank ("https://www.ncbi.nlm.nih.gov/") in its version of Jun. 3, 2020. The UniProt and/or NCBI GenBank identification numbers of the disclosed terpene synthases are provided herein in table 1. By reference, the amino acid sequences of such protein entries of the terpene synthases of the invention are incorporated herein by reference. The term "unmodified wild type terpene synthase" as used in the context of this invention shall refer to any of the proteins listed in table 1.

TABLE 1

| Protein name | Uniprot Accession Number: | GenBank Accession Number: |
|---|---|---|
| Hydropyrene synthase (HpS) from *Streptomyces clavuligerus* | SCLAV_po765 | WP_003963279 |
| Class I terpene synthase CotB2 from *Streptomyces melanosporofaciens* | COTB2_STRMJ | |
| Diterpene synthase from *Amycolatopsis benzoatilytica* (ABS) | | WP_020663197 |
| Trichodiene synthase from *Fusarium sporotrichioides* | TRI5_FUSSP | |
| Clavulatriene synthase from *Streptomyces clavuligerus* | B5H135_STRCL | |

A modified terpene synthase is preferred, wherein said at least one modified amino acid residue is located in an α-helix structure being part of or close to an active site pocket of the terpene synthase, and wherein said at least one modified amino acid residue is an amino acid with a hydrophobic side chain, such as alanine, valine, isoleucine, leucine, methionine, phenylalanine, tyrosine, or tryptophan, and/or an amino acid with a polar uncharged side chain, such as threonine, cysteine, asparagine, glutamine, or serine. In one preferred embodiment, the present invention pertains to a modified terpene synthase comprising at least one modified amino acid residue as compared to an amino acid sequence of an unmodified wild type terpene synthase, wherein said at least one modified amino acid residue is a substitution of a wild type amino acid residue (or of several wild type amino acid residues) for an amino acid residue (or several amino acid residues, each) having a hydrophobic side chain, such as alanine, valine, isoleucine, leucine, methionine, phenylalanine, tyrosine, or tryptophan, and/or for an amino acid residue (or several amino acid residues, each) having a polar uncharged side chain such as threonine, cysteine, asparagine, glutamine, or serine. In a particularly preferred embodiment, this invention pertains to a modified terpene synthase, wherein said at least one modified amino acid residue is a substitution of a wild type amino acid residue selected from:

(i) methionine at position 71,
(ii) methionine at position 75,
(iii) glycine at position 182,
(iv) histidine at position 184,
(v) methionine at position 300, and
(vi) methionine at position 304, in the amino acid sequence of the unmodified wild type HpS according to SEQ ID NO: 1, or wherein said at least one modified amino acid residue is a substitution of a wild type amino acid residue located at an equivalent position of any of (i) to (vi) in the amino acid sequence of an unmodified wild type terpene synthase according to any one of SEQ ID NOs: 2 to 5. In a particularly preferred embodiment, said at least one modified amino acid residue is a substitution of a wild type amino acid residue selected from (i) M71, (ii) M75, (v) M300 and (vi) M304 in the amino acid sequence of the unmodified wild type HpS according to SEQ ID NO: 1, or wherein said at least one modified amino acid residue is a substitution of a wild type amino acid residue located at an equivalent position of any of (i), (ii), (v) and (vi) in the amino acid sequence of an unmodified wild type terpene synthase according to any one of SEQ ID NOs: 2 to 5.

Thus, particularly preferred is at least one modified amino acid residue selected from any of the residues (i) to (vi) in the HpS active site, or the active site of a terpene synthase according to any of the terpene synthases according to any one of SEQ ID NOs: 2 to 5, that are essential to reroute product formation from HP to IE. These residues allow selective formation of biosynthetic pseudopterosin precursors IE A and B in an *Escherichia coli* host. Catalytic active methionines of Trichodiene synthase from *Fusarium sporotrichioides* have been disclosed in Dixit et al., 2017.[3]

Yet another particularly preferred embodiment relates to a modified terpene synthase, wherein the modified terpene synthase comprises at least one substitution selected from the group consisting of:

(i) a substitution of methionine for tyrosine at position 71,
(ii) a substitution of methionine for phenylalanine at position 75,
(iii) a substitution of methionine for leucine at position 75,
(iv) a substitution of glycine for alanine at position 182,
(v) a substitution of glycine for phenylalanine at position 182,
(vi) a substitution of histidine for alanine at position 184,
(vii) a substitution of histidine for phenylalanine at position 184,
(viii) a substitution of methionine for isoleucine at position 300,
(ix) a substitution of methionine for isoleucine at position 304,
(x) a substitution of methionine for threonine at position 304, and
(xi) a substitution of methionine for cysteine at position 304, in the amino acid sequence of the unmodified wild type HpS according to SEQ ID NO: 1, or wherein said modified terpene synthase comprises at least one substitution at an amino acid residue located at an equivalent position of any of (i) to (xi) in the amino acid sequence of an unmodified wild type terpene synthase according to any one of SEQ ID NOs: 2 to 5.

Particularly preferred modified terpene synthases according to this invention are listed in Table 2:

| Number of HpS mutant | SEQ ID No. | Substitution numbering |
|---|---|---|
| 1 | 8 | (i) |
| 2 | 9 | (ii) |
| 3 | 10 | (iii) |
| 4 | 11 | (iv) |
| 5 | 12 | (v) |
| 6 | 13 | (vi) |
| 7 | 14 | (vii) |
| 8 | 15 | (viii) |
| 9 | 16 | (ix) |
| 10 | 17 | (x) |
| 11 | 18 | (xi) |

In all aspects and embodiments of the present invention it may be preferred that the modified terpene synthase comprises an amino acid sequence according to any one of SEQ ID Nos. 8 to 18. Further preferred is a modified terpene synthase having at least 75% sequence identity to an amino acid sequence according to any one of SEQ ID Nos. 8 to 18, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence according to any one of SEQ ID Nos. 8 to 18. Another preferred embodiment, which can be combined with any aspect and/or specific embodiment of this invention, relates to a modified terpene synthase consisting of an amino acid sequence according to any one of SEQ ID Nos. 8 to 18. In a preferred embodiment, a modified terpene synthase having at least 75% sequence identity, or more, to an amino acid sequence according to any one of SEQ ID NO: 8 to 18, has the same or similar activity as a modified terpene synthase according to any one of SEQ ID NO: 8 to 18 in the sense that such modified terpene synthase having at least 75% sequence identity is also a "modified terpene synthase", as defined herein.

Further preferred is the modified terpene synthase, wherein the amino acid sequence of said modified terpene synthase further comprises one or more amino acid deletions, substitutions, and/or additions at positions other than at position 71, 75, 182, 184, 300, and/or 304 according to the amino acid sequence of the unmodified wild type terpene synthase according to SEQ ID NO: 1, or other than the at least one substitution at said equivalent position of an unmodified wild type terpene synthase according to any one of SEQ ID NOs: 2 to 5. In a preferred embodiment, such modified terpene synthase further comprising one or more amino acid deletions, substitutions and/or additions at positions other than at position 71, 75, etc. . . . , is functionally still a "modified terpene synthase", as defined herein.

Yet another aspect of this invention, which can be combined with any number of the disclosed and/or preferred embodiments and/or aspects of this invention, then relates to a nucleic acid, encoding for a modified terpene synthase according to this invention.

A further aspect of this invention, which can be combined with any of the disclosed and/or preferred embodiments and/or aspects of this invention, relates to an expression vector capable of expressing the nucleic acid of this invention.

As used herein, the term "vector" refers to a DNA construct comprising a DNA sequence to be operably linked to a suitable control sequence that can express DNA inside a host cell. A vector may be a plasmid, a phage particle, or a latent genomic insert. When a vector is transformed into a suitable host, it may be replicated or functioned regardless of a host genome, or in some cases, it may be integrated into a genome itself. A plasmid is most generally used as a vector, and thus plasmid and vector are sometimes used interchangeably in the present invention. However, the present invention also includes other types of vectors having the same function as the function that is known or is to be known in the art.

A nucleic acid is operably linked when it is arranged with a functional relationship with other nucleic acid sequences. It may be a gene and control sequence(s) that is linked in a process that enables the gene expression when a proper molecule is linked to the control sequence(s). As an example, a promoter or an enhancer is operably linked to a coding sequence when affecting transcription of a sequence; a ribosome binding domain is operably linked to a coding sequence when affecting transcription of a sequence; or a ribosome binding domain is operably linked to a coding sequence when it is arranged to be easily translated. Generally, the term "operably linked" refers to a contact of a linked DNA sequence, or that the secretion leader is contacted and presented in the leading frame. However, the enhancer is not required to contact.

The term "expression vector" as used in the present invention generally refers to a double-strained DNA fragment as a general recombinant carrier inserted with a recombinant DNA fragment. Recombinant DNA shall refer to heterogeneous DNA that is natively undiscovered DNA in a host cell. The expression vector is inside the host cell, can be replicated regardless of host chromosome DNA, and may produce several copies of a vector and (recombinant) DNA inserted in the same.

In the present invention, the recombinant vector may be various vectors comprising a plasmid vector, a bacteriophage vector, a cosmid vector, and a yeast artificial chromosome (YAC) vector. A typical plasmid vector that can be used for the object of this invention has a structure comprising (a) a replication origin that allows a replication to be effectively performed to include hundreds of plasmid vectors per host cell, (b) an antibiotic-resistance gene that allows a host cell transformed with a plasmid vector to be selected, and (c) a restriction site of restriction enzyme that can be inserted with a foreign DNA fragment. Even if there is no suitable restriction site of a restriction enzyme, a vector and foreign DNA may be easily ligated when using the linker and the synthetic oligonucleotide adaptor according to a general method.

Another aspect of this invention, which can be combined with any number of the disclosed and/or preferred embodiments and/or aspects of this invention, pertains to a recombinant host cell comprising the modified terpene synthase, the nucleic acid, or the expression vector according to this invention. In all aspects of this invention, the host cell is preferably a bacterial cell or a yeast cell. However, the present invention is not limited thereto.

Yet another aspect of this invention, which can be combined with any number of the disclosed and/or preferred embodiments and/or aspects of this invention relates to a method for producing a modified terpene synthase according to this invention, the method comprising culturing the host cell that comprises the modified terpene synthase, or expresses the nucleic acid, or comprises the expression vector according to this invention, and isolating the modified terpene synthase from the host cell or its culture medium.

Another aspect of this invention, which can be combined with any number of the disclosed and/or preferred embodiments and/or aspects of this invention, pertains to the use of a modified terpene synthase, a nucleic acid, an expression vector, or a host cell, for the production of at least one pseudopterosin intermediate, such as Elisabethatriene, Isoelisabethatriene A, Isoelisabethatriene B, Erogorgiaene, or Seco-Pseudopterosin, and/or for the production of at least one pseudopterosin, such as Pseudopterosin A. Said use is preferably an in vitro or in vivo use, more preferably an in vitro use.

Yet another aspect of this invention, which can be combined with any of the disclosed and/or preferred embodiments and/or aspects of this invention relates to a method for producing at least one pseudopterosin intermediate, such as Elisabethatriene, Isoelisabethatriene A, Isoelisabethatriene B, Erogorgiaene, or Seco-Pseudopterosin, and/or for producing at least one pseudopterosin, such as Pseudopterosin A, the method comprising the steps of:

a) Providing an intermediate generated from a Geranylgeranyl pyrophosphate (GGPP);
b) Providing a modified terpene synthase comprising at least one modified amino acid residue as compared to the amino acid sequence corresponding to an unmodified wild type terpene synthase according to any one of SEQ ID NOs: 1 to 5, wherein said at least one modified amino acid residue is located in an α-helix structure being part of or close to an active site pocket of the terpene synthase, and wherein said at least one modified amino acid residue is an amino acid with a hydrophobic side chain, such as alanine, valine, isoleucine, leucine, methionine, phenylalanine, tyrosine, or tryptophan, and/or an amino acid with a polar uncharged side chain, such as threonine, cysteine, asparagine, glutamine, or serine, and
c) Destabilizing the intermediate of step a) by said at least one modified amino acid residue of the modified terpene synthase, thereby producing at least one pseudopterosin intermediate, such as Elisabethatriene, Isoelisabethatriene A, Isoelisabethatriene B, Erogorgiaene, or Seco-Pseudopterosin, and/or for producing at least one pseudopterosin, such as Pseudopterosin A.

As a first step, an intermediate generated from a Geranylgeranyl pyrophosphate (GGPP) is provided. Most preferably, this intermediate has been generated by 1,10-ring closing of a GGPP molecule, wherein said 1,10-ring closing shifts the carbocation of said GGPP to position C11. Thus, the term "an intermediate generated from a Geranylgeranyl pyrophosphate (GGPP)", as provided in step a) of the method, shall preferably refer to a 1,10-ring closed intermediate generated from a Geranylgeranyl pyrophosphate (GGPP).

Additionally, preferred is a method, further comprising the step of:

d) 1,3-hydride migrating the intermediate as generated in step c), wherein said 1,3-hydride migrating shifts the carbocation of said intermediate to position C7. The additional step d) of the method preferably shifts the product range towards Isoelisabethatrienes.

A further preferred embodiment relates to a method of this invention, wherein said method further comprises the steps of:

e) Performing a 1,2-hydride shift of an intermediate as generated in step d), and f) Deprotonating an intermediate as generated in step e), thereby producing Isoelisabethatriene A.

Another preferred embodiment of this invention pertains to a method of this invention, wherein said method further comprises the step of:

e) Deprotonating an intermediate as generated in step d), thereby producing Isoelisabethatriene B.

A particularly preferred embodiment relates to a method of this invention, wherein said method further comprises converting Isoelisabethatriene A to Erogorgiaene, and/or converting Isoelisabethatriene B to 1R-Epoxy-elisabetha-5,14-diene.

Yet another further preferred embodiment relates to a method of this invention, wherein said method further comprises the step of modifying said at least one pseudopterosin intermediate, such as Elisabethatriene, Isoelisabethatriene A, Isoelisabethatriene B, Erogorgiaene, or Seco-Pseudopterosin, and/or said at least one pseudopterosin, such as Pseudopterosin A, wherein said modifying preferably comprises a modification selected from a functionalization, oxidation, hydroxylation, methylation, glycosylation, lipid-conjugation, or any other natural or synthetic modification, or combinations thereof.

This invention further pertains to a chemo-enzymatic oxidation that selectively transforms isoelisabethatriene A and B to the advanced pseudopterosin precursor erogorgiaene and the new compound 1R-epoxy-elisabetha-5,14-diene (EED), respectively. To generate advanced pseudopterosin precursors, IE A and B were subjected to a lipase-mediated chemo-enzymatic oxidation. Under identical conditions IE A and B displayed differential reactivity, leading to the formation of the established pseudopterosin precursor erogorgiaene and the new natural product 1R-epoxy-5,14-elisabethadiene, respectively. Generally, oxyfunctionalisation of diterpenoid backbones provides access to a wide chemical space that enables diversified functionalisation approaches, the basis for the efficient chemo-enzymatic production of various bioactive compounds. Given the diversity of functionalised serrulatane diterpenes, this development is the basis for the efficient chemoenzymatic production of such bioactive compounds. The concerted application of different biotechnological and chemical functionalisation strategies towards 1R-epoxy-5,14-elisabethadiene functionalisation provides a route for development of designed bioactive natural products.

Notably, the chemical synthesis of erogorgiaene requires at least eight steps, utilizing petroleum-based building blocks, the biotechnological approach provides a stereoselective, two-step biosynthetic procedure, solely based on renewable feedstocks. Furthermore, in contrast to chemical synthesis this method does not require metal organic catalysts, nor does it result in any toxic side streams, and it is carried out under mild reactions conditions, thereby featuring a superior ecological profile. This consolidated and sustainable production route enables a fast-track pharmaceutical development pipeline for erogorgiaene. As few antibiotic drug leads have been developed to clinical maturity in the past decades, the scalable erogorgiaene supply route addresses an urgent need in the pharmaceutical industry, that underpins new drug development. Such developments are essential to protect an ever-increasing global population from rapidly emerging contagious epidemics (e.g. tuberculosis).

In all aspects and embodiments of the present invention it may be preferred that the terpene synthase used in step b) of the above methods is a modified Hydropyrene synthase (HpS), a bacterial diterpene synthase from *Streptomyces clavuligerus* comprising the amino acid sequence according to SEQ ID NO: 1, a class I terpene synthase, such as CotB2 from *Streptomyces melanosporofaciens* comprising the amino acid sequence according to SEQ ID NO: 2, a diterpene synthase, such as the diterpene synthase from *Amycolatopsis benzoatilytica* (ABS) comprising the amino acid sequence according to SEQ ID NO: 3, a Trichodiene synthase from *Fusarium sporotrichioides* comprising the amino acid sequence according to SEQ ID NO: 4, or a Clavulatriene synthase, such as Clavulatriene synthase from *Streptomyces clavuligerus*, comprising the amino acid sequence according to SEQ ID NO: 5.

Another preferred aspect of this invention pertains to a pseudopterosin intermediate, such as Elisabethatriene, Isoelisabethatriene A, Isoelisabethatriene B, Erogorgiaene, or Seco-Pseudopterosin, and/or a pseudopterosin, such as Pseudopterosin A, produced by the above method.

Interestingly, pseudopterosin intermediates, such as Elisabethatriene, Isoelisabethatriene A, Isoelisabethatriene B, Erogorgiaene, or Seco-Pseudopterosin, and/or a pseudopterosins, such as Pseudopterosin A, produced by any of the methods of this invention, show a different conformation in their chiral positions compared to naturally occurring pseudopterosin intermediates and/or pseudopterosins, such as those harvested and extracted from its natural source, i.e. the gorgonian coral *A. elisabethae*. Coral-derived pseudopterosin intermediates and/or pseudopterosins are characterized by a (+)-conformation, while the pseudopterosin intermediates, such as Elisabethatriene, Isoelisabethatriene A, Isoelisabethatriene B, Erogorgiaene, or Seco-Pseudopterosin, and/or a pseudopterosins, such as Pseudopterosin A, produced by any of the methods of this invention are characterized by a (−)-conformation. Thus, the naturally occurring pseudopterosin intermediates and/or pseudopterosins are epimers at location C11 of the pseudopterosin intermediates and/or pseudopterosins produced by the methods of this invention. Importantly, the pseudopterosin intermediates and/or a pseudopterosins produced by any of the methods of this invention are biologically active, and have, for example, anti-inflammatory, anti-biotic, anti-viral and/or analgesic activity.

Yet another preferred aspect of this invention relates to a kit comprising:

(i) a modified terpene synthase, a nucleic acid, an expression vector, a host cell, or a pseudopterosin intermediate and/or a pseudopterosin according to this invention;

(ii) written instructions to apply said modified terpene synthase, nucleic acid, expression vector, host cell, pseudopterosin intermediate and/or pseudopterosin, and (iii) optionally, a container holding said modified terpene synthase, nucleic acid, expression vector, host cell, pseudopterosin intermediate and/or pseudopterosin, and said written instructions.

Also preferred is a kit for producing at least one pseudopterosin intermediate, such as Isoelisabethatriene A, Isoelisabethatriene B, Erogorgiaene, or Seco-Pseudopterosin, and/or for producing at least one pseudopterosin, such as Pseudopterosin A, comprising:

i) a host cell, optionally wherein said host cell comprises Geranylgeranyl pyrophosphate (GGPP);

ii) optionally, GGPP; and iii) a modified terpene synthase according to this invention, wherein said modified terpene synthase catalyzes the production of said at least one pseudopterosin intermediate and/or said at least one pseudopterosin from GGPP in said host cell in an amount that is greater than the amount of the same pseudopterosin intermediate and/or the same pseudopterosin produced from GGPP by the unmodified wild type terpene synthase having the amino acid sequence set forth in any one of SEQ ID NOs: 1 to 5 in the same host cell and under the same conditions.

Another aspect of the invention then pertains to a pseudopterosin intermediate or the pseudopterosin for use in medicine. The pseudopterosin intermediate or the pseudopterosin according to this invention can be used to treat and/or prevent a large number of diseases.

Yet another aspect of this invention relates to the use of a pseudopterosin intermediate and/or a pseudopterosin according to this invention in the treatment and/or prevention of an inflammatory disease, a bacterial disease, a viral disease, a rheumatic disease, a skin disease, and/or pain, or in the manufacture of a medicament against an inflammatory disease, a bacterial disease, a viral disease, a rheumatic disease, a skin disease, and/or pain. The pseudopterosin intermediate and/or the pseudopterosin according to this invention has anti-inflammatory and analgesic activities, and can be used, for example, as a non-steroidal anti-inflammatory drug (NSAID) and antibiotic. The pseudopterosin intermediates or the pseudopterosins according to this invention can further be applied in first line-treatments to control contagion agents and diseases associated with excessive inflammatory response during infective epidemics (i.e. COVID-19). Moreover, these pseudopterosin type compounds can be applied in chronic inflammatory diseases. The IE A oxidation product erogorgiaene has potent antibacterial activity against antibiotic sensitive and multi drug resistant *M. tuberculosis* strains (MICs: 32.25 μg/ml and 125.00 μg/ml, respectively). Thus, Erogorgiaene can be used as antibiotic.

Beyond the generation of new antibiotic entities, erogorgiaene enables consolidated (bio)chemical synthesis to afford Pseudopterosin-type anti-inflammatory drugs. To that end, pseudopterosin could serve as a new first-line treatment option in controlling excessive inflammatory symptoms in newly evolving viral epidemics (e.g. COVID-19) as well as treating chronic inflammation in aging, industrial populations. Ultimately, a sustainable pseudopterosin production platform will also replace coral extracts in scalable cosmetic applications, thereby preventing exploitation of fragile reef eco-systems, while protecting marine biodiversity. In summary, the technology presented in this invention simultaneously addresses four of 17 UN sustainability goals (Good Health and Well-being (Goal 3), Climate Action (13), Protecting aquatic (15) and terrestrial (15) life), thereby signaling a path to enhance resilience towards global challenges such as climate change and evolving infectious diseases.

In a further aspect of this invention, a pharmaceutical composition comprising a pseudopterosin intermediate and/or a pseudopterosin, and a pharmaceutically active carrier and/or excipient, is provided.

An additional aspect of this invention pertains to a compound for use in the treatment and/or prevention of an inflammatory disease, a bacterial disease, a viral disease, a rheumatic disease, a skin disease, and/or pain, wherein said compound comprises a pseudopterosin intermediate and/or a pseudopterosin, or a pharmaceutical composition according to this invention.

In a preferred embodiment, said compound for use is provided in form of a gel, an ointment, a salve, a cream, a tablet, a pill, a capsule, a troche, a dragée, a powder, an aerosol spray, a nasal spray, a suppository, and/or a solution.

Another aspect relates to a method of treatment and/or prevention of a an inflammatory disease, a bacterial disease, a viral disease, a rheumatic disease, a skin disease, and/or pain in a subject, the method comprising the step of administering to the subject a therapeutically effective amount of a pseudopterosin intermediate and/or a pseudopterosin, a pharmaceutical composition, or a compound for use according to this invention.

In all aspects and embodiments of the present invention it may be preferred that said subject is a mammal, such as a human, a mouse, rat, guinea pig, rabbit, cat, dog, monkey, or preferably a human, for example a human patient, more preferably a human patient suffering from an inflammatory disease, a bacterial disease, a viral disease, a rheumatic disease, a skin disease, and/or pain.

Further preferred is the above method of treatment, wherein said therapeutically effective amount of said pseudopterosin intermediate, pseudopterosin, pharmaceutical composition, and/or compound for use is administered to said subject by oral, transdermal (topical), intravenous, vaginal, intranasal, intrathecal, intra-arterial, intradermal, subcutaneous, intracerebroventricular, intraparenchymal, intratumoral, transmucosal, rectal, bronchial, and/or parenteral administration, or by any clinically/medically accepted method.

In another preferred embodiment, said therapeutically effective amount of said pseudopterosin intermediate, pseudopterosin, pharmaceutical composition, and/or compound for use is provided in form of a gel, an ointment, a salve, a cream, a tablet, a pill, a capsule, a troche, a dragée, a powder, an aerosol spray, a nasal spray, a suppository, and/or a solution.

Yet another aspect of this invention, which can be combined with any of the disclosed and/or preferred embodiments and/or aspects of this invention, relates to the use of a pseudopterosin intermediate and/or a pseudopterosin according to this invention for cosmetic purposes, such as for anti-aging cosmetic purposes. Particularly preferred is the use of a pseudopterosin intermediate and/or a pseudopterosin derived from any of the methods according to this invention for cosmetic purposes, such as for anti-aging cosmetic purposes.

The terms "of the [present] invention", "in accordance with the invention", "according to the invention" and the like, as used herein are intended to refer to all aspects and embodiments of the invention described and/or claimed herein.

As used herein, the term "comprising" is to be construed as encompassing both "including" and "consisting of", both meanings being specifically intended, and hence individually disclosed embodiments in accordance with the present invention. Where used herein, "and/or" is to be taken as specific disclosure of each of the two specified features or components with or without the other. For example, "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

BRIEF DESCRIPTION OF THE FIGURES

The figures show:

FIG. 3 shows conserved motifs of class I terpene synthases with their respective catalytic function ($Mg^{2+}$-coordinating residues in bold) and the corresponding amino acid sequences for CotB2 and HpS.

FIG. 10: Sequence alignment CotB2 (residues 24-296 of SEQ ID NO: 2) and HpS (SEQ ID NO: 26). The boxes are used as a code for identical and/or similar amino acids, as well as amino acids with no corresponding match. The following code is used: Identical amino acids are highlighted by the following Box.

Highly similar amino acids are highlighted by the following

Box.

Similar amino acids are highlighted by the following

Box

Amino acids with no corresponding match are highlighted by the following

Box.

Figure 11:
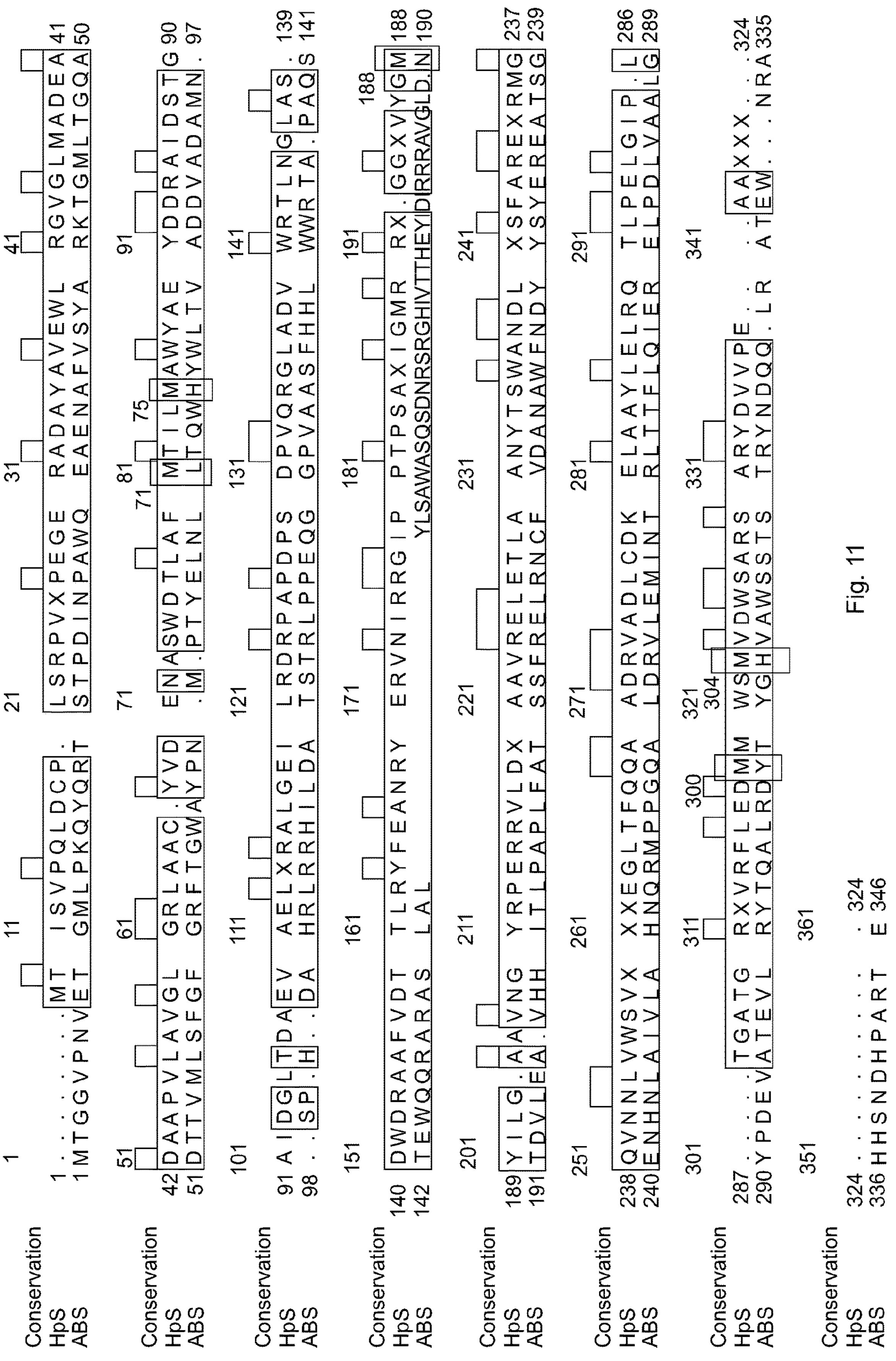

FIG. 11: Sequence alignment of HpS (SEQ ID NO: 27) and ABS (SEQ ID NO: 28). Conserved residues are highlighted by a squared box on top of the aligned sequences

EXAMPLES

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

The examples show:

Example 1: HpS Model-Based Mutagenesis Strategy

Figure 1:
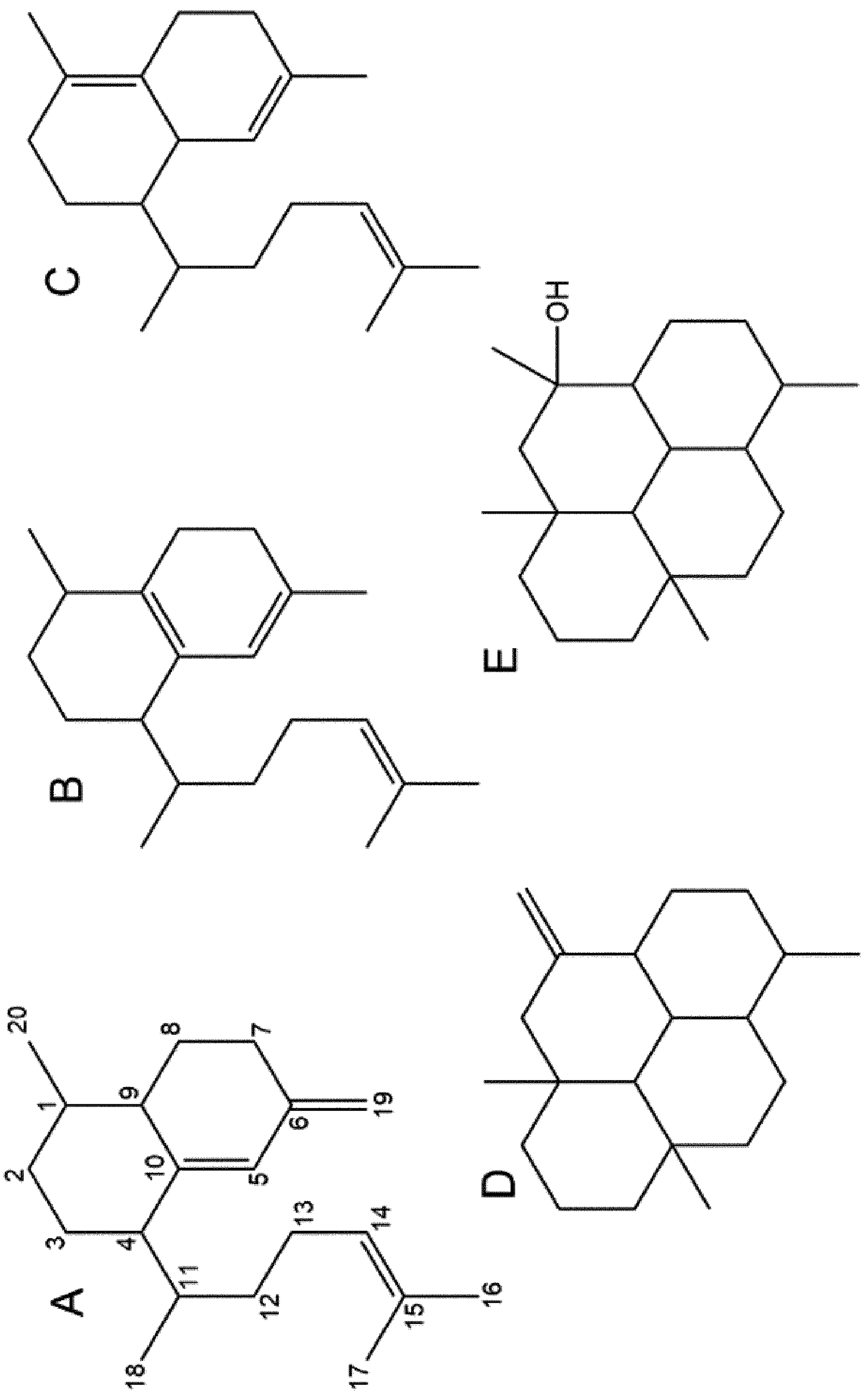
FIG. 1 shows structures of elisabethatriene (A), IE A (B), IE B (C), HP (D) and HPol (E); B (12%), C (9%), D (52%) and E (26%) are products of the hydropyrene synthase (HpS) (percentage of product spectrum of wild-type HpS in brackets; carbon numbering as previously described by Kohl and co-workers 4).

Previous studies reported the formation of early pseudopterosin precursors IE A and B by wild-type (wt) HpS, but with low yields. Initial in vitro studies with HpS revealed a plausible cyclisation mechanism for GGPP conversion towards the products IE A, IE B, HP and HP-ol (FIG. 1). None of these previous studies specifically aimed for selective production of pseudopterosins' precursors IE A and IE B.

Knowledge-based HpS structure-function studies require a model to delineate a consolidated mutagenesis strategy. Thus, a homology model of the closed complex of HpS synthase was generated by applying the Web tool I-Tasser (https://zhanglab.ccmb.med.umich.edu/I-TASSER/). The predicted structure was further analysed and modified within the environment of UCSF Chimera software package including Modeller software package for comparative modelling (http://www.cgl.ucsf.edu/chimera/). As previously described by Hirte et al., all substrate docking studies were predicted by AutoDock Vina.[5,6] For comparative alignment of secondary structure of terpene synthases HHPred applying HMM/HMM comparisons and Ali2D including PSIPRED and MEMSAT software package was used.[7]

While class I terpene synthases, such as HpS, share low primary sequence similarity, these enzymes display a significant homology in secondary and tertiary structural features, forming a common α-barrel protein scaffold. Class I terpene synthase catalysis is primed by initial binding and orientation of GGPP via its diphosphate (PP) moiety to a conserved $Mg^{2+}$ triade in the active site, characterised by the canonical (DDXX(X)D) motif, and which is located in the centre of the α-barrel. Substrate binding initiates active site closure by an induced fit mechanism and subsequent $Mg^{2+}$-mediated PP hydrolysis, generating a highly reactive, priming carbocation. Solvent water is expelled during active site closure creating a hydrophobic microenvironment that prevents an uncontrolled nucleophilic attack on the carbocation. Moreover, specific amino acid residues lining the active site also pre-shape the priming carbocation, thereby significantly influencing the terminal terpene product profile. The inventors reasoned that for subsequent site directed mutagenesis of residues in proximity (3-8 Å) to the docked substrate replacement by more polar or more spacious non-polar residues should allow for quenching of the carbocation intermediate and restrict free folding of the HP skeleton.

The subsequent intramolecular carbocation rearrangement cascade and terminal cyclization can then commence through C1-C6-, C1-C7-, C1-C10-, C1-C11-, C1-C14- or C1-C15-bond forming reactions, which are modulated by the relative double bond reactivity of the priming carbocation. In addition to the inherent carbocation reactivity, the local electrostatic environment created by the substrate-derived PP moiety, as well as transient electronic and ionic interactions with amino acids of the active site, drive and control successive carbocation rearrangements along the reaction trajectory towards an enzyme specific terminal product profile. Specifically, terminal cyclisation is induced by amino acid-mediated deprotonation or addition of a water molecule to the final carbocation. These concerted enzyme-substrate interactions facilitate an intense diversity of stereochemically complex diterpene macrocycles, all being derived from the universal precursor GGPP.

As no HpS crystal structure is available, a homology model was constructed, employing the high resolution crystal structure of the taxonomically and secondary structure-related[7] (FIG. 10) class I terpene synthase CotB2 (PDB-ID 6GGI) from *Streptomyces melanosporofaciens* as a template. The *Streptomyces*-derived diterpene synthase CotB2, which converts GGPP via cyclooctat-9-en-7-ol to the anti-inflammatory agent cyclooctatin, belongs to the best characterized diterpene synthases to date. CotB2, catalysing the cyclization of GGPP to tricyclic cyclooctat-9-en-7-ol, has been subject to extensive mutagenesis studies. To date, CotB2 is the only class I (di)terpene synthase, for which a closed, catalytically relevant structure containing a trapped diterpene reaction intermediate, is available. Computational interrogation of this unique structure in synergy with extensive QM/MD simulations provided detailed insights into the dynamic CotB2 reaction mechanism, highlighting a concerted network of catalytically essential amino acid lining its active site. Therefore, CotB2 represents an ideal template for a comprehensive HpS structure-function analysis.

An initial CotB2/HpS structural comparison indicated that all catalytically relevant class I structural motifs are conserved (FIG. 3). However, the canonical class I DDXXD motif, responsible for initial binding and orientation of the substrate's (GGPP) diphosphate (PP) moiety in the active site, is altered in both CotB2 and HpS to DDXD ($^{110}$DDMD) and DDXXXD ($^{82}$DDRAID), respectively. Interestingly, such extensive modifications of the highly conserved DDXXD motif are rare in class I terpene synthases (TPSs). However, the addition of a single amino acid (X) has also been reported in other TPSs, such as selina-3,7(11)-diene synthase ($^{82}$DDGYCE) and (+)-T-muurolol synthase ($^{83}$DDEYCD). Other active site motifs are also conserved in HpS and CotB2 (FIG. 3 and FIG. 10), including the NSE triad and the class I TPS specific WXXXXXRY motif. The CotB2 and HpS-specific amino acid sequences for each catalytically relevant motif are listed in FIG. 3.

Interestingly, a more extensive HpS structural interrogation revealed the distinctive presence of five unique methionine residues ($^{71}$M, $^{75}$M, $^{188}$M, $^{300}$M and $^{304}$M) inside or in the immediate vicinity of the putative HpS active site. A feature that has not been reported or experimentally evaluated for any TPS. The catalytic relevance of these residues is largely unknown, although a computational (QM) study of *Fusarium sporotrichioides* trichodiene synthase (TdS) implicates a methionine residue in interactions with TdS-specific carbocation reaction intermediates. Thus, these methionine residues were included in the mutational strategy to elucidate HpS structure-function relationships to selectively establish the biosynthetic pseudopterosin precursors IE A and B as the main GGPP cyclisation products.

Relevant active site residues selected for mutagenesis are listed in Table 3.

TABLE 3

Comparison of HpS and CotB2 active site residues used to delineate the HpS mutagenesis strategy. Amino acid residues were chosen due to their potential to alter the product range or stabilize the carbocation intermediate. Residues in bold show identical amino acids in HpS and CotB2.

| HpS | Cot B2 | HpS | Cot B2 |
|---|---|---|---|
| L 54 | V 80 | G 182 | D 180 |
| Y 58 | S 84 | H 184 | G 182 |
| M 71 | V 99 | M 188 | W 186 |
| M 75 | N 103 | M 300 | L 281 |
| Y 78 | T 106 | M 304 | N 292 |
| A 79 | F 107 | W 307 | W 288 |
| Y 153 | F 156 | R 313 | R 294 |
| R 179 | R 177 | | |

The relevant active site residues selected for mutagenesis listed in table 3 include $^{307}$W and $^{313}$R residues of the conserved $^{307}$WXXXXXXRY motif. Conservative substitutions of these residues in CotB2 have previously been shown to modulate the product spectrum.

Example 2: Tailoring *E. coli* for HpS-Derived Diterpene Production

An engineered *E. coli* host harbouring a metabolically balanced two-plasmid terpene production system was employed for HpS expression, which allows for rapid mutagenesis of wt class I HpS and subsequent screening for altered product profiles.[8] For terpene extraction, technical grade ethanol, ethyl acetate and hexane were purchased from Westfalen AG (Minster, Germany). For all other purposes, highest purity grade chemicals were used. Acetonitrile, ethyl acetate, hexane, methanol, propionic acid, and media components were obtained from Roth chemicals (Karlsruhe, Germany). Immobilized Lipase B from *C. antarctica* (CalB), $CDCl_3$, Benzene-$d_6$ and urea hydrogen peroxide were purchased from Sigma-Aldrich (St. Louis, USA).

*E. coli* strain DH5a was used for plasmid generation and cloning. It was cultivated at 37° C. in Luria-Bertani medium. Terpenes were produced with *E. coli* strain ER2566. During shaking flask experiments *E. coli* ER2566 was grown at 23° C. in either Luria-Bertani or R-Media supplemented with 30 g $L^{-1}$ glucose and 5 g $L^{-1}$ yeast extract. In case of fermentation experiments, *E. coli* ER2566 was cultivated in R-Media supplemented with 30 g $L^{-1}$ glycerol and 5 g $L^{-1}$ yeast extract. Chloramphenicol (30 μg $mL^{-1}$) and Kanamycin (50 μg $mL^{-1}$) were added as required.

All genes encoding diterpene synthase (Uniprot: SCLAV_p0765) from *S. clavuligerus* (ATCC 27064) were cloned into pACYC-based expression vector system. All genes and primers were synthesized by Eurofins Genomics GmbH (Ebersberg, Germany). Genes were codon-optimised for *E. coli* by use of the GeneOptimizer™ software.

Overnight pre-culture was used to inoculate the fermenters of a DASGIP® 1.3 L parallel reactor system (Eppendorf AG, Germany) ($OD_{600}$=0.1). Cultivation temperature was kept constant at 23° C. Stirring velocity, airflow, oxygen content and feeding protocol were set as previously described.[8] Feed solution consisted of 600 g $L^{-1}$ glycerol, 5 g $L^{-1}$ yeast extract, 35 g $L^{-1}$ collagen, 20 g $L^{-1}$ $MgSO_4$, 0.3 g $L^{-1}$ Thiamine-HCl, 5 ml $L^{-1}$ 1M Ammonium iron(III) citrate, 20 ml $L^{-1}$ 100× trace elements solution (pH=7.0) as described previously.[8] To monitor terpene production, samples were taken at different time points.

Figure 2:
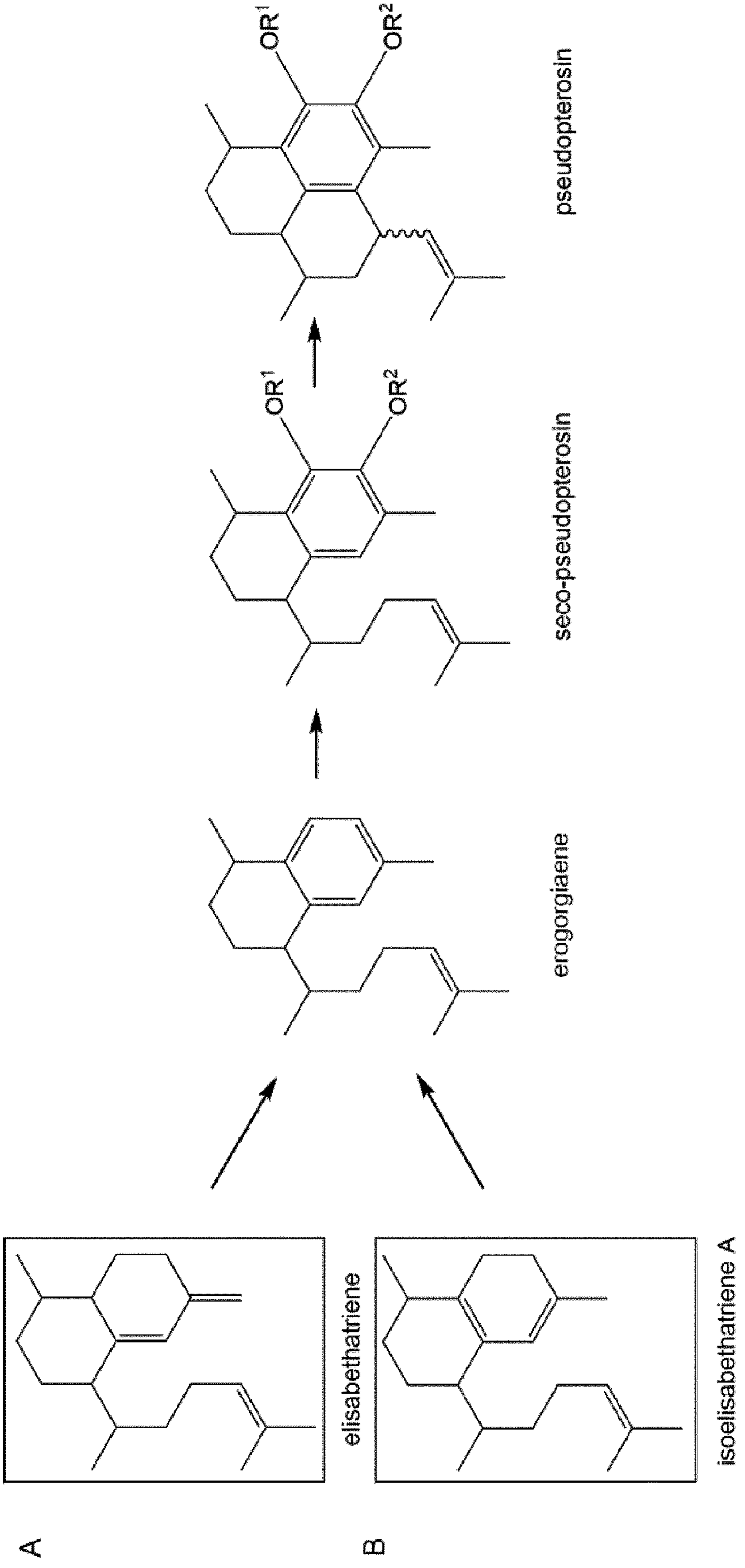
FIG. 2 shows early biosynthetic intermediates leading to pseudopterosins; (A) endogenous coral pathway of pseudopterosin production starting with elisabethatriene via erogorgiaene and seco-pseudopterosins; (B) Proposed pathway using HpS from *S. clavuligerus* encompassing isoelisabethatriene A; R1,2=sugar moiety.

Co-transformation of the plasmid carrying the codon-optimised HpS gene, together with a separate plasmid harbouring bottleneck enzymes of *E. coli* terpene biosynthesis, led to efficient production of functional HpS. The balanced carbon flux and terpene precursor supply in the tailored *E. coli* host allowed native HpS to efficiently convert GGPP to HP, HP-ol, IE A and IE B (total terpene yield 55.56 f 2.01 mg/l, FIG. 2). The HpS-harbouring *E. coli* production system provided rapid and simplified cultivation with high product yields.

Example 3: Diterpene-Directed Product Screening of HpS Variants

The inventors reasoned that for subsequent site directed mutagenesis of residues in proximity (3-8 Å) to the docked substrate replacement by more polar or more spacious non-polar residues should allow for quenching of the carbocation intermediate and restrict free folding of the HP skeleton. A tailored design of the active site of an enzyme allows the generation of a hydrophilic environment, thereby enabling water molecules access to the active site. As a result, the water molecules in the active site can quench a carbocation, whereby a hydroxyl group at the active site is generated. A library of HpS mutants (FIG. 4) was expressed in *E. coli*, and diterpene products were extracted from the cultivation broth.[8] To extract products and other compounds from shaking flask experiments and samples taken from fermentation units an equivalent volume of solvent (ethanol: ethyl acetate:hexane=1:1:1) was added to the culture broth and mixed for 2 h at room temperature. The solution was centrifuged for 5 min at 8000 rpm to separate the upper organic phase to be analysed by GC-FID and GC-MS.

The whole fermentation broth was extracted by addition of the same volume of ethanol. The first process step was carried out on a rotary shaker (80 rpm) at 20° C. for 12 h. Subsequently, the extraction mixture was centrifuged for 20 min at 7000 rpm to separate the supernatant from the cell debris. Via addition of ethyl acetate (50% of supernatant volume) a second extraction step on the rotary shaker (80 rpm) was started (20° C. for 5 h). After 5 hours the same amount of hexane was added, and the extraction process continued for further 2 h. Finally, the phases were separated by a separation funnel and the organic phase was evaporated.

The flash chromatography system PLC 2250 (Gilson, USA) allowed for a separation between the fatty acid residues and the terpene fraction. To this end, the solvents hexane (A) and ethyl acetate (B) were pumped with a flowrate of 10 mL $min^{-1}$ at room temperature over a Luna 10 μm Silica (2) 100A column. The following gradient was applied: 100% A for 15 min, increasing B in one step to 100%, holding 100% B for 15 min and then applying 100% A for 30 min. Eluted compounds were analysed by a diode array and an ELSD detector which was flushed with nitrogen gas at 40° C. Fractions of interest were reduced by nitrogen flow to approximately 2 ml. Terpene concentration was measured using GC-FID. Fractions containing IEs were mixed with acetonitrile (ACN). Subsequently hexane and ethyl acetate were carefully evaporated until only acetonitrile remained.

To further purify the IEs dissolved in ACN, the samples were injected into an Ultimate 3000 UHPLC system (Thermo Scientific, USA) containing a binary pump, a diode array detector, an automated fraction collector, and a Jetstream b1.18 column oven. Separation of isoelisabethatrienes from hydropyrenol, hydropyrene and other terpene derivatives (maximum terpene content of 25 mg) was carried out at 30° C. oven temperature using $H_2O$ (A) and ACN (B) as solvents with a flowrate of 2.2 mL $min^{-1}$ on a NUCLEODUR® C18 HTec 250/10 mm 5 μm column with a guard column NUCLEODUR® C18 HTec 10/8 mm and guard column holder 8 mm (Macherey-Nagel GmbH & Co. KG, Germany). The separation gradient started with 30% B for 5 min, then it increased within 55 min to 1000% B. 100% B was maintained for further 60 min.

To separate IE A from B, the same HPLC system was equipped with a NUCLEODUR® C18 Isis 250/10 mm 5 μm column with guard column NUCLEODUR® C18 Isis 10/8 mm and guard column holder 8 mm (Macherey-Nagel GmbH & Co. KG, Germany). The mobile phase consisted of $H_2O$ (A) and MeOH (B). The following program was applied: 30% B for 5 min, then increase to 100% B within 55 min to remain for another 35 min. The oven temperature was set to 30° C. After liquid-liquid extraction with hexane purified compounds were stored at −20° C.

Analysis and quantification of terpenes was performed using a Trace GC-MS Ultra system with DSQII (Thermo Scientific, USA). One microliter (1/10 split) of sample was injected by a TriPlus auto sampler onto a SGE BPX5 column (30 m, I.D 0.25 mm, film 0.25 μm) with an injector temperature of 280° C. Helium was used as carrier gas with a flow rate of 0.8 ml/min. Initial oven temperature was set to 50° C. for 2 min. The temperature was increased to 320° C. at a rate of 10° C./min and then held for 3 min. MS data were recorded at 70 eV (EI). Masses were recorded in positive mode in a range between 50 and 650. GC-FID analysis was performed in the same way.

Compounds for NMR studies were dissolved either in $CDCl_3$ or benzene-$d_6$. $^{13}C$ NMR spectra were measured with a Bruker Avance-III 500 MHz spectrometer equipped with a cryo probe head (5 mm CPQNP, 1H/13C/31P/19F/29Si; Z-gradient). $^1H$ NMR spectra as well as the 2D experiments (HSQC, HMBC, COSY, NOESY) were obtained on an Avance-I 500 MHz system with an inverse probehead (5 mm SEI, $^1H/^{13}C$; Z-gradient). The temperature was set to 300 K. Resulting data was processed and analysed by TOPSPIN 3.0 or MestreNova. Chemical shifts were given in ppm relative to $CDCl_3$ (S=7.26 ppm for $^1H$ and 6=77.16 ppm for $^{13}C$ spectra) or benzene-d-$_6$ (S=7.16 ppm for $^1H$ and 6=128.06 ppm for $^{13}C$ spectra). The total terpene yields of catalytically viable HpS mutants was comparable to that of the wild type enzyme. Subsequently, all enzyme mutants were evaluated for variations in their product spectrum with respect to wt HpS. A specific focus was given to enhanced IE A and/or B generation.

Figure 4:
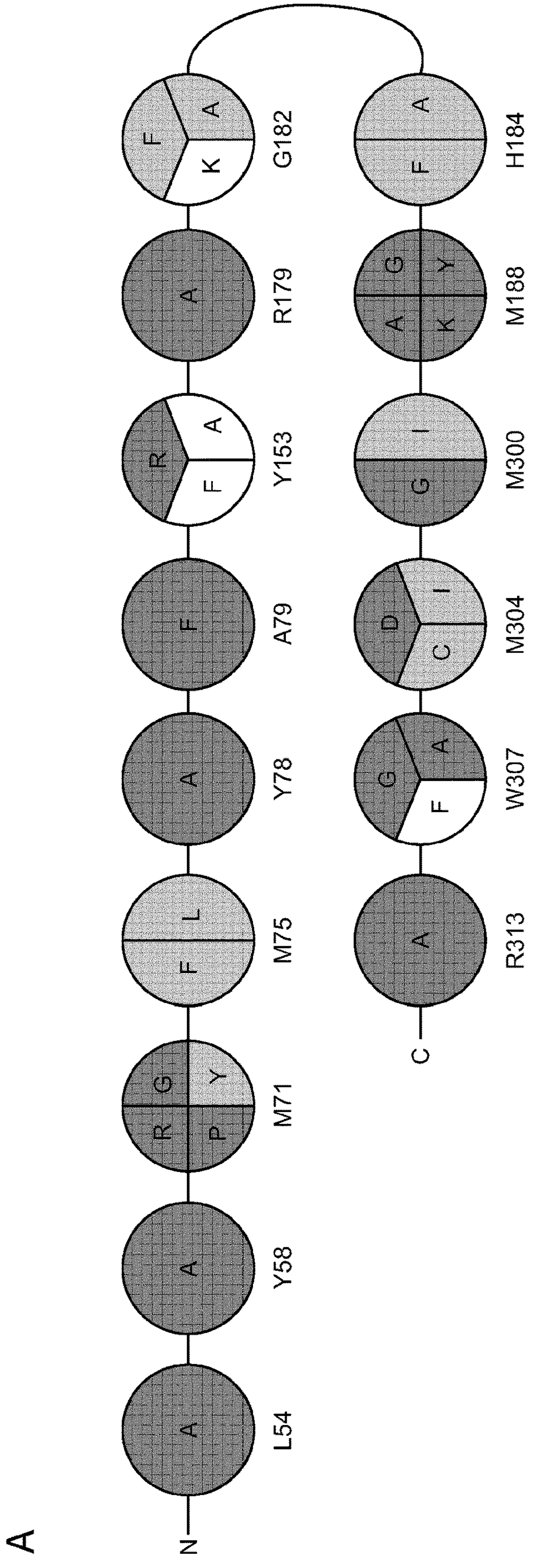
FIG. 4 shows (A) Variants linked to respective mutation sites (white: variants with wild type-like product spectrum; dark grey: inactive variants; light grey: variants with altered product spectrum); (B) Secondary structure of HpS with highlighted mutation sites. (C) Secondary structure of HpS with highlighted mutation sites, tilted 90° compared to the structure in B. (D) Primary structure and secondary structure elements of HpS (cylinders and lines indicate alpha helices and beta sheets, respectively; dots indicate mutation sites, wherein the code corresponds to the amino acid code of (C) and (D) (SEQ ID NO: 1); highlighted parts of the primary structure show conserved motifs (DDXXD, NSE; WXXXXXRY).
Figure 4:
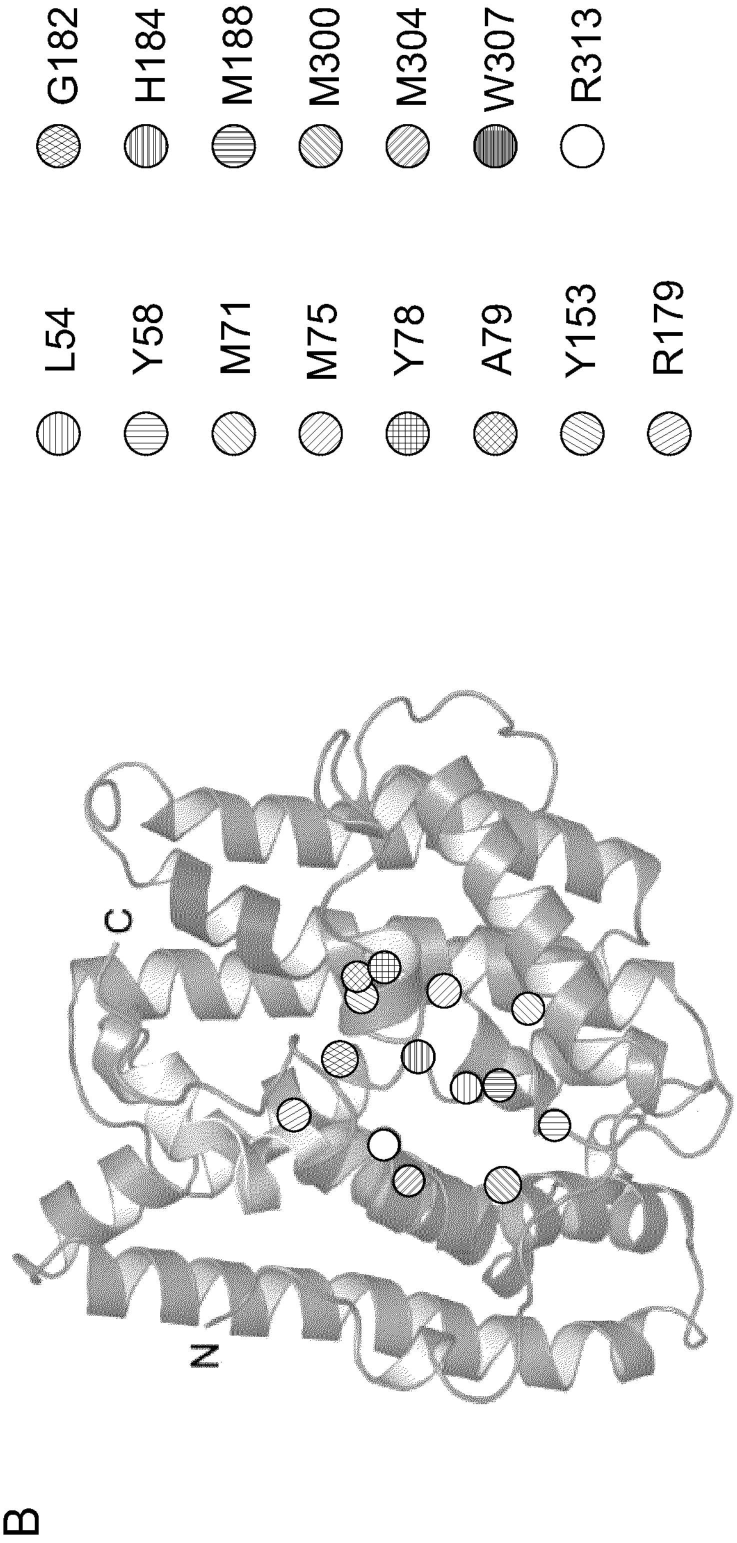
Figure 4:
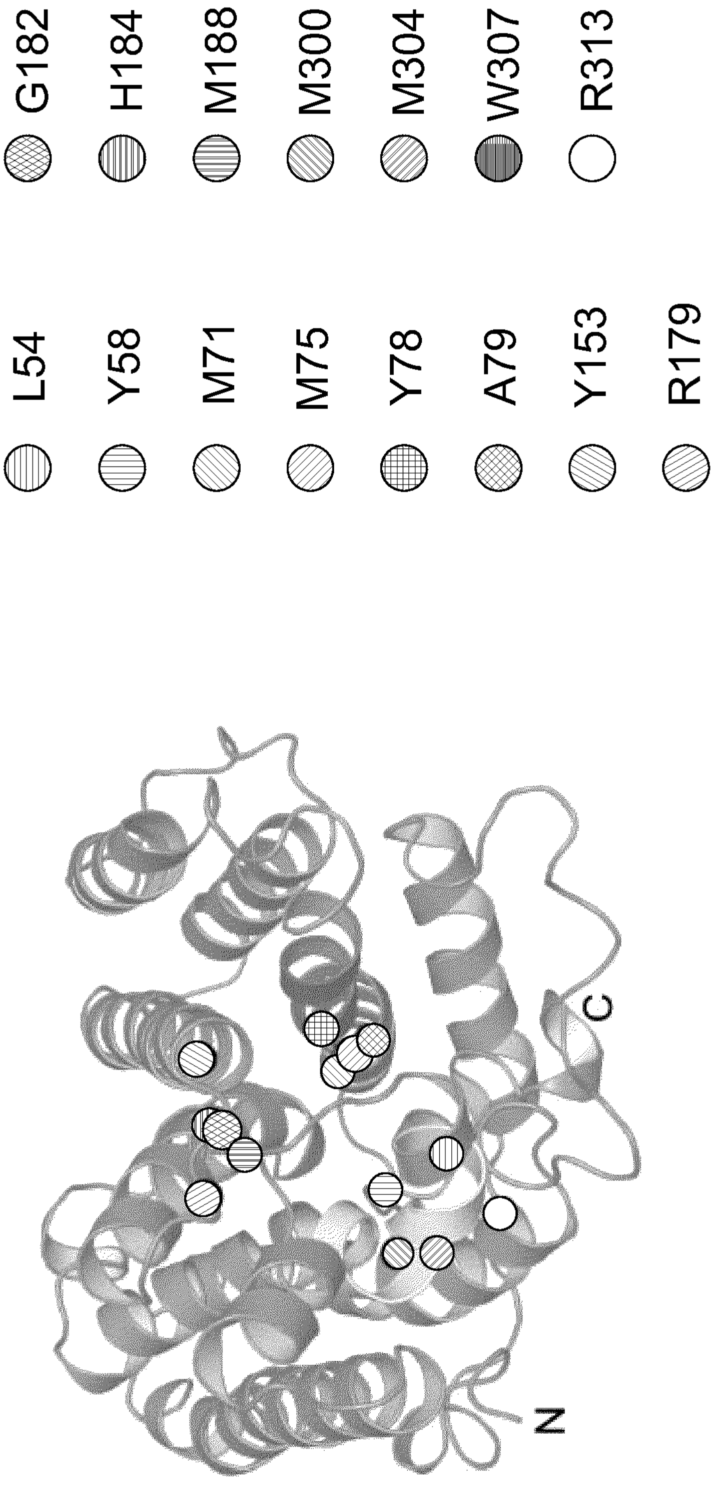
Figure 4:
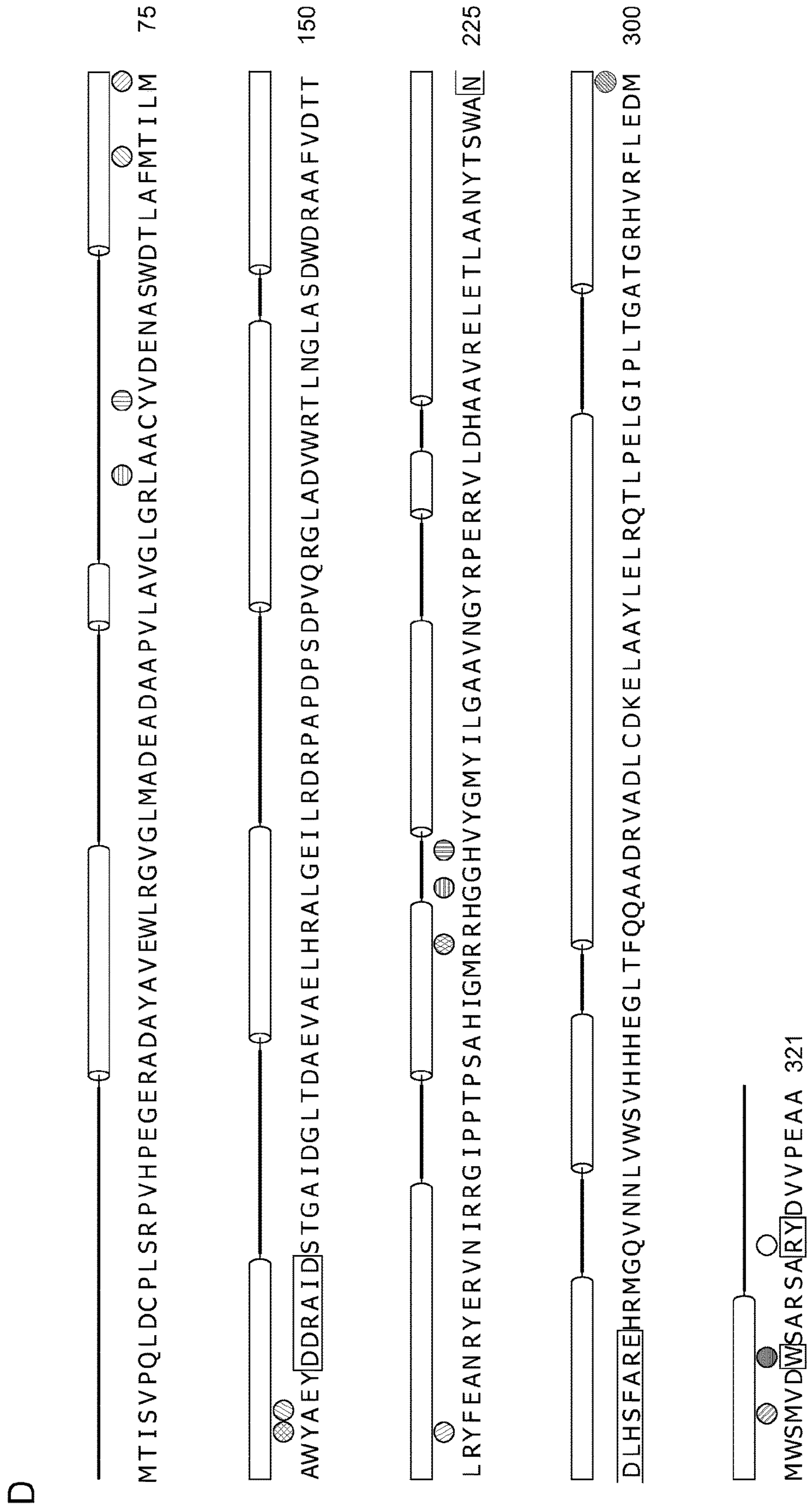

Mutations Y153A, Y153F, G182K, and W307F did not affect the product spectrum. In contrast, mutations L54A, Y58A, M71R, M71P, M71G, Y78A, A79F, Y153R, R179A, M188G, M188A, M188K, M188Y, M300G, M304D, W307A, W307G and R313A inactivated HpS, indicating that the mutated amino acids are essential for catalysis. Most notably, variants M71Y, M75F, M75L, G182A, G182F, H184A, H184F, M300I, M304I and M304C displayed an altered product spectrum with respect to wt HpS (FIG. 4). Mutation $^{179}R$, $^{307}W$ and $^{313}R$ either resulted in a non-active variant or displayed the native HpS product spectrum. Therefore, $^{179}R$, $^{307}W$ and $^{313}R$ are likely to be essential for catalysis, which is consistent with previous reports for CotB2.

Figure 5:
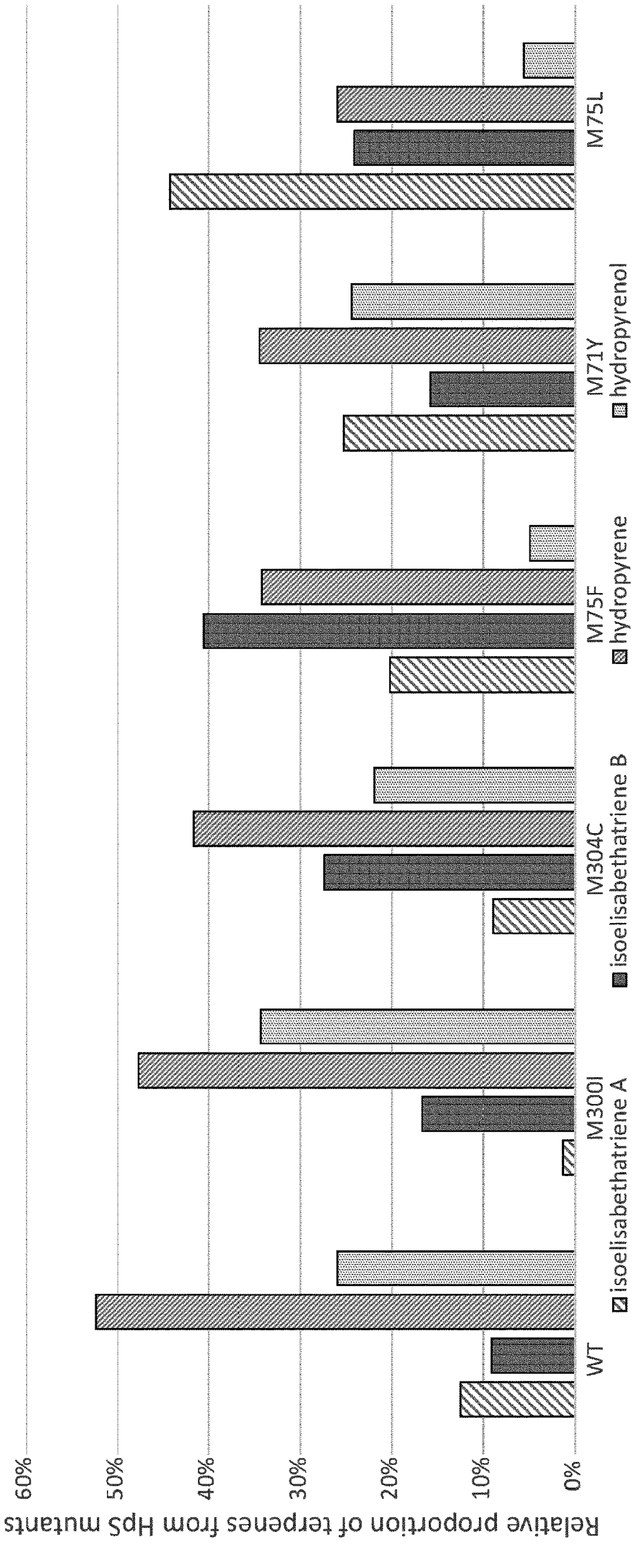
FIG. 5 shows the relative proportion of the main products of the reaction catalysed by HpS and its variants (displayed as percental ratio of the areas of the respective GC-FID product peaks); HpS variants displayed in order of increasing IE A content.

Interestingly, mutants M71Y, M75F, M75L, M300I, and M304C targeting HpS-specific methionine residues displayed the most pronounced shifts in the diterpene product profile when compared to wt HpS (FIG. 5). Mutations M300I and M304C lead to a decrease in IE A production and a concomitant increase in IE B. A more significant effect is observed for mutations M71Y, M75F and M75L. Each variant displays a significantly enhanced yield of IE A and B, with a concomitant reduction in HP and HPol production. The most prominent effect is observed for mutations of M75. Notably, M75F showed the highest IE B yield, whereas M75L displayed the highest IE A yield.

Since IE A is a biosynthetic pseudopterosin intermediate[24], its increased yield in the M71Y, M75F and M75L variants is highly encouraging for the ongoing effort to generate a sustainable pseudopterosin production platform. Mutants M75F and M75L shifted the product spectrum towards an IE isomer as their major product. M75L is the most promising mutation for pseudopterosin production due to its particularly high IE A yield. Therefore, this HpS variant was termed isoelisabethatriene synthase (IES) and used for all downstream efforts to generate advanced pseudopterosin intermediates.

Figure 6:
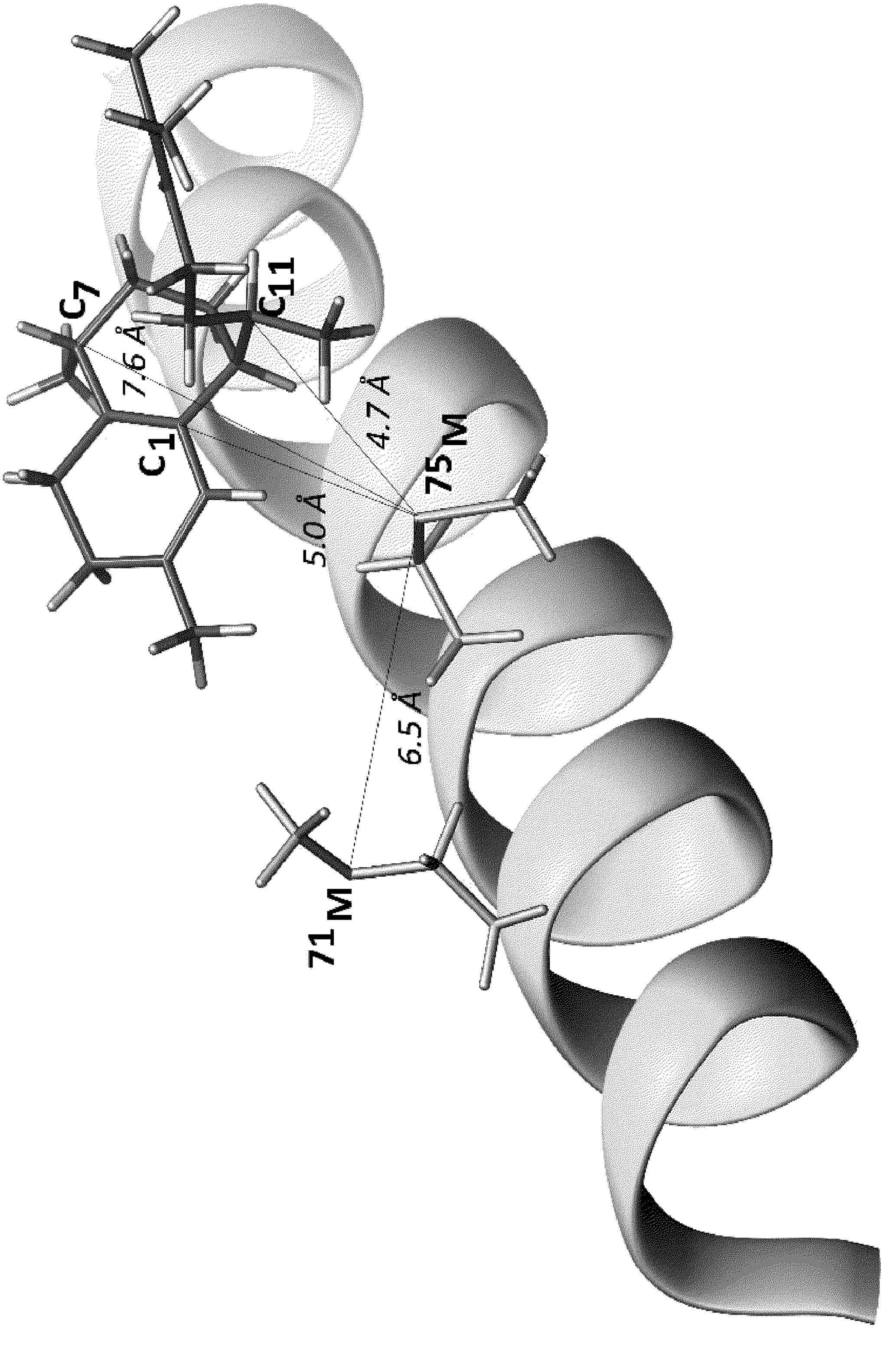
FIG. 6 shows a structural model of catalytically active residues in HpS. Distance of 75M to catalytically important carbocations C1 (5.0 Å), C11 (4.7 Å) and C7 (7.6 Å), as well as to 71M (6.5 Å; putatively active as dative bond). The numbering of carbon atoms in the intermediate is based on the numbering of GGPP.

Example 4: In Silico Driven Mechanistic Considerations for IE Generating Mutants As mutations of $^{71}M$ and $^{75}M$ significantly modulated the HpS product spectrum towards IE production it was essential to evaluate the chemical mechanisms that induce these effects. Interestingly, no methionine-carbocation interactions within a distance of ~8 Å have been suggested to be important in the catalytic mechanism of CotB2. Notably, the residue equivalent to $^{75}M$ in HpS is $^{103}N$ in CotB2. The latter was proposed to coordinate a water molecule that terminates the CotB2 cyclization cascade or form a dipole-charge interaction during the cyclization reaction. Interestingly, the N103A variant CotB2 featured a 3,7,12-dolabellatriene as the major cyclisation product. CotB2 has one methionine ($^{189}M$) that lines its active site but whose replacement by cysteine does not directly interfere with catalysis. The only report that describes the effect of a metionine on terpene synthase catalysis is a computational study of trichodiene synthase, in which 73M is stabilizing selected carbocation conformations via a dative sulphur-carbocation bond. Hence, substrate tumbling, and premature deprotonation is prevented. It is thus plausible that methionine residues (especially $^{75}M$) in HpS also aid in the stabilization of carbocation intermediates, providing a route which is crucial for opening a distinct reaction pathway (e.g. en-route to HP derivatives; FIG. 6). Therefore, mutagenesis of $^{71}M$ and $^{75}M$ in HpS can reroute GGPP cyclisation to either HP or IE derivatives.

Figure 7:
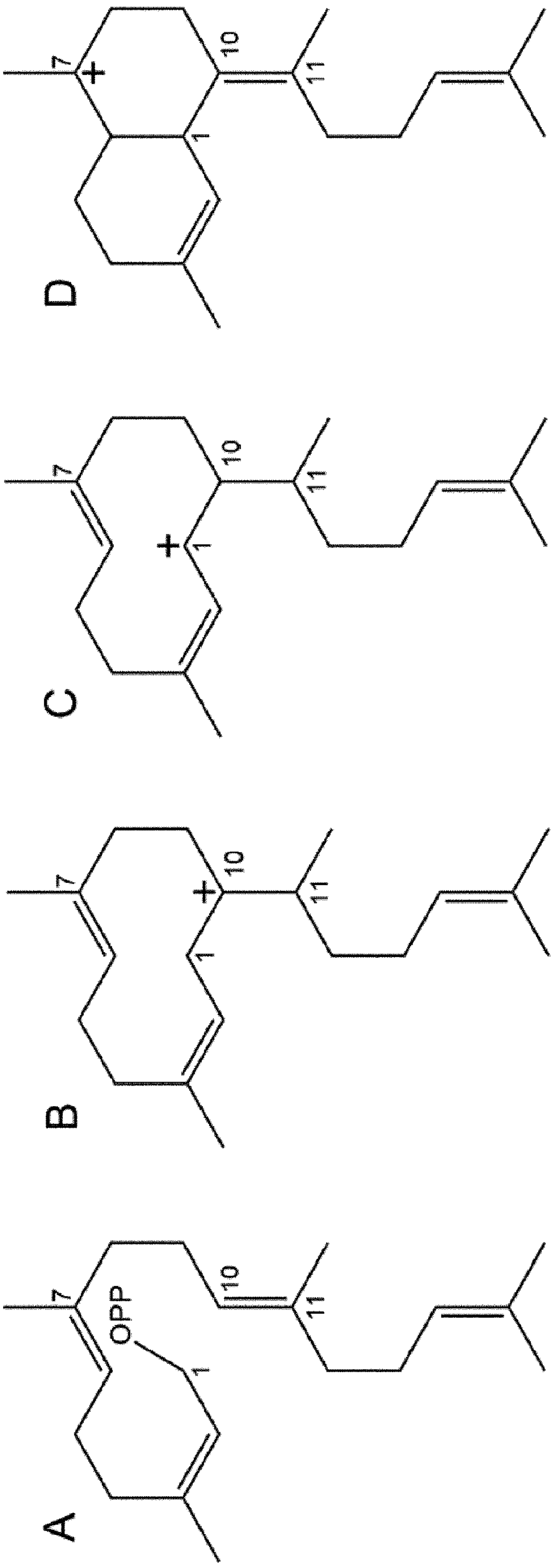
FIG. 7 shows important cyclisation intermediates; (A) GGPP; (B) C10 carbocation intermediate; (C) C1 carbocation intermediate (D): C7 carbocation intermediate; numbering of carbon atoms based on numbers of GGPP.

The initial cyclisation step of the HpS-specific mechanism for GGPP cyclisation to HP, HP-ol, IE A and IE B comprises a 1,10-ring closure, which generates a carbocation at C11. Subsequently, the carbocation (FIG. 7) can be channeled in two distinct reaction pathways. The primary route proceeds via the stable Markovnikov C11 carbocation followed by a 1,3-hydride shift to form the less stable anti-Markovnikov C1 carbocation, which ultimately provides HP or HPol, respectively. In contrast, the formation of IE derivatives requires a 1,3-hydride migration, forming a carbocation at position C7, which leads either to IE A via a 1,2-hydrid shift and deprotonation or to IE B via simple deprotonation. For effective biotechnological pseudopterosin precursor supply, it is crucial to evolve the product spectrum of HpS towards a specific production of IE isomers. As the C11 carbocation is the essential intermediate for changing the preferred pathway to the desired IE A, it is crucial to prevent the 1,3-hydrid shift towards the less stable anti-Markovnikov C1 carbocation.

The route towards HP derivative formation requires that the anti-Markovnikov C1 carbocation is stabilized within the active site. In wild-type HpS $^{75}$M is in close proximity (~5.0 Å) to both C1 and C11 carbons, and it is plausible that in the C1:C11 carbocation transition the proximal $^{71}$M plays a stabilizing role via a dative Met-Met interaction (FIG. 6). Hence, the performed mutagenesis of $^{71}$Met and $^{75}$Met are likely destabilizing the key C1 intermediate and therefore showing a significant product shift towards Isoelisabethatriene A and B.

Example 5: Identification of Hydroxylated IE Derivatives

While IE A and B are primary biosynthetic pseudopterosin precursors, especially the oxidised IE A forms represents advanced pseudopterosin precusors. Culture broth extracts of *E. coli* expressing IES were evaluated for the presence of oxidised IE derivatives using a GC-MS based screening method. Inspection of GC-MS spectra identified a compound with MS spectral similarity to IE but with extended retention time (retention time (Rt) (IE A): 20.46 min; Rt (IE B): 20.87 min; Rt (unknown compound): 22.28 min) and an parent ion mass (m/z) of 290, indicating the presence of a hydroxyl-moiety (data not shown). The putative hydroxylated IE derivative can potentially arise by controlled water capture within the HpS active site, which facilitates carbocation quenching along the reaction trajectory. Analogous data have been reported for the class I germacradien-4-ol sesquiterpene synthase.

Moreover, the presence of the aromatized IE derivative, erogorgiaene, a key intermediate in coral-based pseudopterosin biosynthesis, was confirmed by comparison with an authentic GC-MS standard isolated from *A. elisabethae* coral tissue. However, as erogorgiaene could not be detected, when the *E. coli* extract was analysed directly after the extraction process, it is plausible that oxygen exposure of the analysed extract initiated an oxidative transformation of IE A or B to erogorgiaene. As erogorgiaene is an advanced intermediate in pseudopterosin biosynthesis, the current data are consistent with previous reports indicating that hydroxylated elisabethatriene derivatives are direct erogorgiaene precursors in the pseudopterosin biosynthetic pathway.

Example 6: Chemo-Enzymatic IE A and B Oxidation—a Route to Advanced Pseudopterosin Precursors As erogorgiaene formation is a crucial step in pseudopterosin biosynthesis, its definitive biosynthetic origin was probed by development of a selective in-vitro chemoenzymatic oxidation approach with IE A and B as substrates. Recently, selective functionalization of the macrocyclic diterpene hydrocarbons dolabellatriene and taxadiene via lipase-mediated oxidation reactions has been reported.[8] Consequently, in a lipase-mediated and chemo-enzymatic assay IE A and B were oxidized to establish whether oxyfunctionalization, and therefore activation of the IE hydrocarbon skeleton, is part of the pseudopterosin biosynthetic pathway.

250 μg $mL^{-1}$ IE A or B was mixed in 5 mL ethyl acetate with 1 μl concentrated propionic acid, 2 mg $mL^{-1}$ immobilised CalB and 2 mg $mL^{-1}$ urea-hydrogen peroxide. Reaction was performed at 22° C. and 1000 rpm in a thermo shaker (Eppendorf AG; Germany). At different time points, samples were taken to monitor the reaction progress by GC-MS analysis.

CalB reaction was stopped at appropriate time points by separation of immobilised CalB from reaction mixture by filtration. The remaining solution was diluted with hexane (1:4) and filtrated through filter paper. Final product purification occurred in two steps:

In case of IE A, the reaction mixture was first purified by flash chromatography. Hence, the solvents hexane (A) and ethyl acetate (B) were applied at 10 mL $min^{-1}$ to a Luna 10 μm Silica (2) 100A column. After 10 min 100% A, solvent B was increased within 5 min to 100%. Finally, another 30 min the system was operated with 100% A. Subsequently, the fractions were further purified by a preparative HPLC system equipped with a NUCLEODUR® C18 HTec 250/10 mm 5 μm column with Guard column NUCLEODUR® C18 HTec 10/8 mm and guard column holder 8 mm (Macherey-Nagel GmbH & Co. KG, Germany). The method used an oven temperature of 30° C. and the solvents $H_2O$ (A) and ACN (B) at a flowrate of 2.2 mL $min^{-1}$. The gradient started with 30% B for 5 min to increase afterwards to 100% B within 55 min. This solvent level was maintained for 60 min.

When purifying products originating from the reaction using IE B, the process also starts with a flash chromatography. This time the gradient was altered to: 1% B for 10 min, increase of B within 41 min to 40%, stay at 40% B for 1 min, further increase to 100% B within the next 3 min and final remain at this level for 10 min. Afterwards the column was cleaned with 100% A for 30 min. Again, the second step consists of a preparative HPLC purification. The solvents remain $H_2O$ (A) and ACN (B), but the following gradient was used: 40% B for 5 min, increase of B to 100% in 30 min and a stay at 100% B for 60 min.

Figure 8:
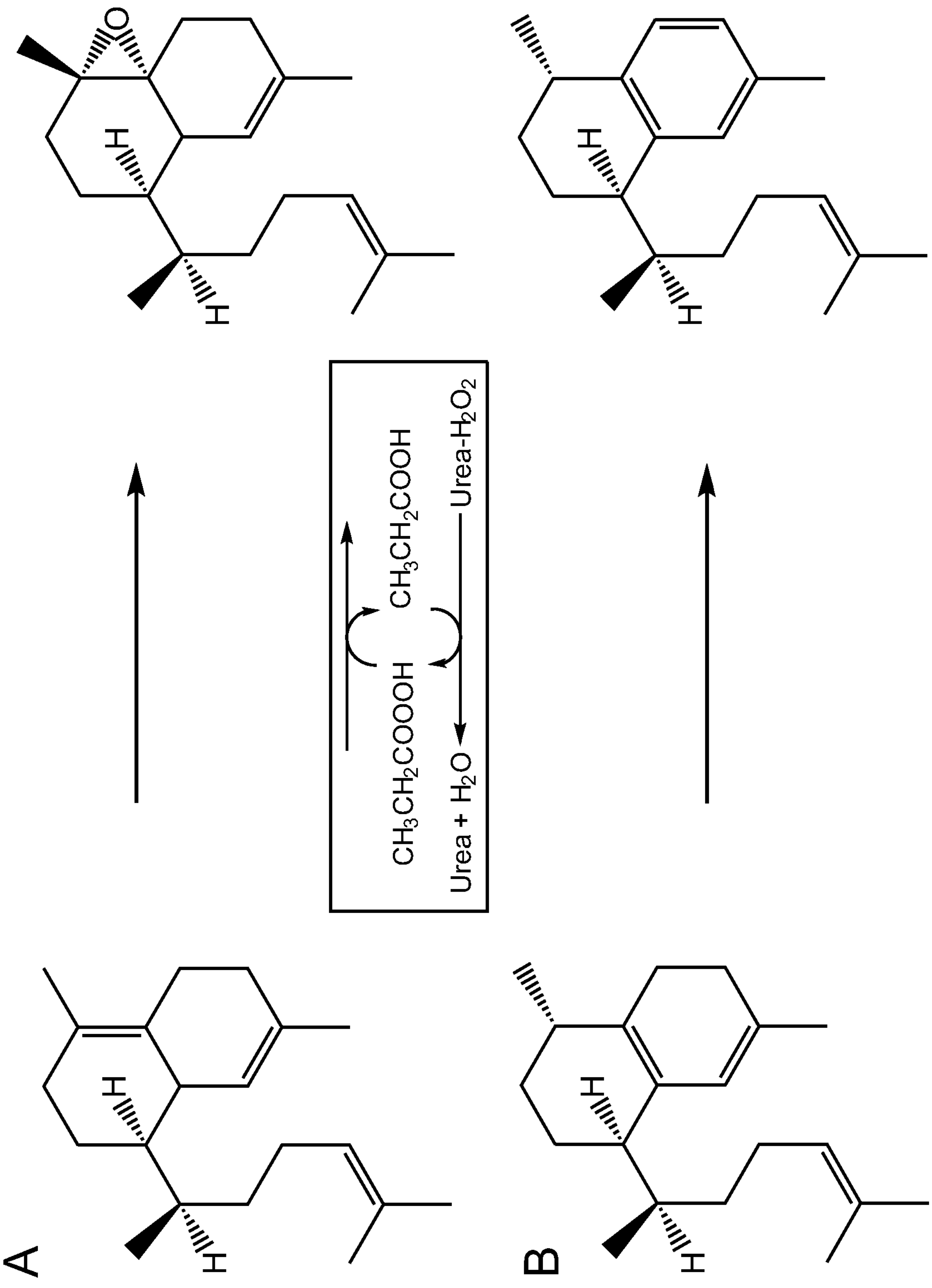
FIG. 8 shows (A) Lipase-mediated epoxidation of IE B to the new natural product 1R-epoxy-5,14-elisabethadiene. (B) Lipase-mediated IE A specific conversion of IE A to (−)-erogorgiaene.

To ensure future process scalability under economic boundary conditions, the inventors employed the industrially well-established lipase Cal B. The mild lipase-mediated IE oxidation was carried out in ethyl acetate in the presence of urea-hydrogen peroxide with propionic acid, which generates the reactive oxidant. The reaction was initiated by in situ generation of per-oxo carboxylic acid as the reactive oxidant, which targets olefinic IE bonds either in re- or si-face conformations to afford a racemic mixture of oxidised products. Reaction progress was monitored by GC-FID analysis, while GC-MS was applied to identify IE A and B specific oxidation products (FIG. 8).

Example 7: Identification of the IE B-Specific Oxidation Products and IE A-Specific Conversion to Erogorgiaene While GC-FID allowed kinetic reaction profiling, parallel GC-MS analysis indicated that the lipase-mediated IE B oxidation resulted in a time dependent formation of IE B mono- (m/z 288) and IE B diepoxides (m/z 304), respectively. To enhance product selectivity towards formation of the IE B mono-epoxide, the reaction was terminated after 120 min (yield of 41%). Subsequently, a 2D-HPLC protocol allowed for 1D and 2D NMR spectroscopy-based structure elucidation of the putative IE B-derived mono-epoxide. $^{13}$C NMR analysis provided characteristic epoxide-type chemical shifts for C1 and C9 at 62.66 and 64.21 ppm, respectively. Comprehensive NMR signal assignment confirmed the IE B monoepoxide as the new natural product 1R-epoxy-5,14-elisabethadiene (EED, FIG. 8).

The epoxidation of the IE B diterpene carbon skeleton enables various downstream biotechnological and chemical functionalization strategies to access a diversified chemical space. As most bioactive terpenoids contain at least one functional group, subsequent modification of EED and other IEs is a fundamental step towards the sustainable generation of new pharmaceutical agents. Various approaches for hydroxyl group functionalization at the bicyclic pseudopterosin carbon skeleton have been applied to generate pseudopterosin derivatives and pseudopteroxazoles, which both were active against *M. tuberculosis* and other pathogens.

Lipase-mediated oxidation rapidly (90 min) transformed IE A into a single new compound (yield: 69%). Synchronous GC-MS analysis indicated that this compound was the aromatic pseudopterosin precursor erogorgiaene (data not shown). For structural confirmation, the putative erogorgiaene was purified via an optimised 2D-HPLC method and subsequently subjected to 1D and 2D NMR spectroscopy. The resulting NMR signals of the purified compound were in agreement with reported data for (+)-erogorgiaene. While NOESY experiments resolved the relative erogorgiaene stereochemistry, the absolute configuration remained elusive. However, the absolute stereochemistry of the primary HpS cyclisation products was previously resolved using isotopically labelled substrates and CD-spectrophotometric cyclisation product detection. The analysis indicated that HpS converts GGPP to the ((−)-IE A enantiomer, while the *A. elisabethae* coral-derived counterpart constitutes (+)-IE A. Similarly, it was deduced that the lipase-based oxidation of HpS derived (−)-IE A leads to the formation of (−)-erogorgiaene, while the coral-derived compound constitutes the (+)-erogorgiaene enantiomer.

The rapid (−)-erogorgiaene formation, precluded observation of any epoxidised IE A intermediates via GC-MS. However, mechanistic considerations imply that (−)-IE A oxidation proceeds via initial epoxidation of the C9-C10 double bond, followed by protonation of the resulting epoxide and a subsequent dehydration, which induces a spontaneous ring system aromatization to afford (−)-erogorgiaene.

Figure 9:
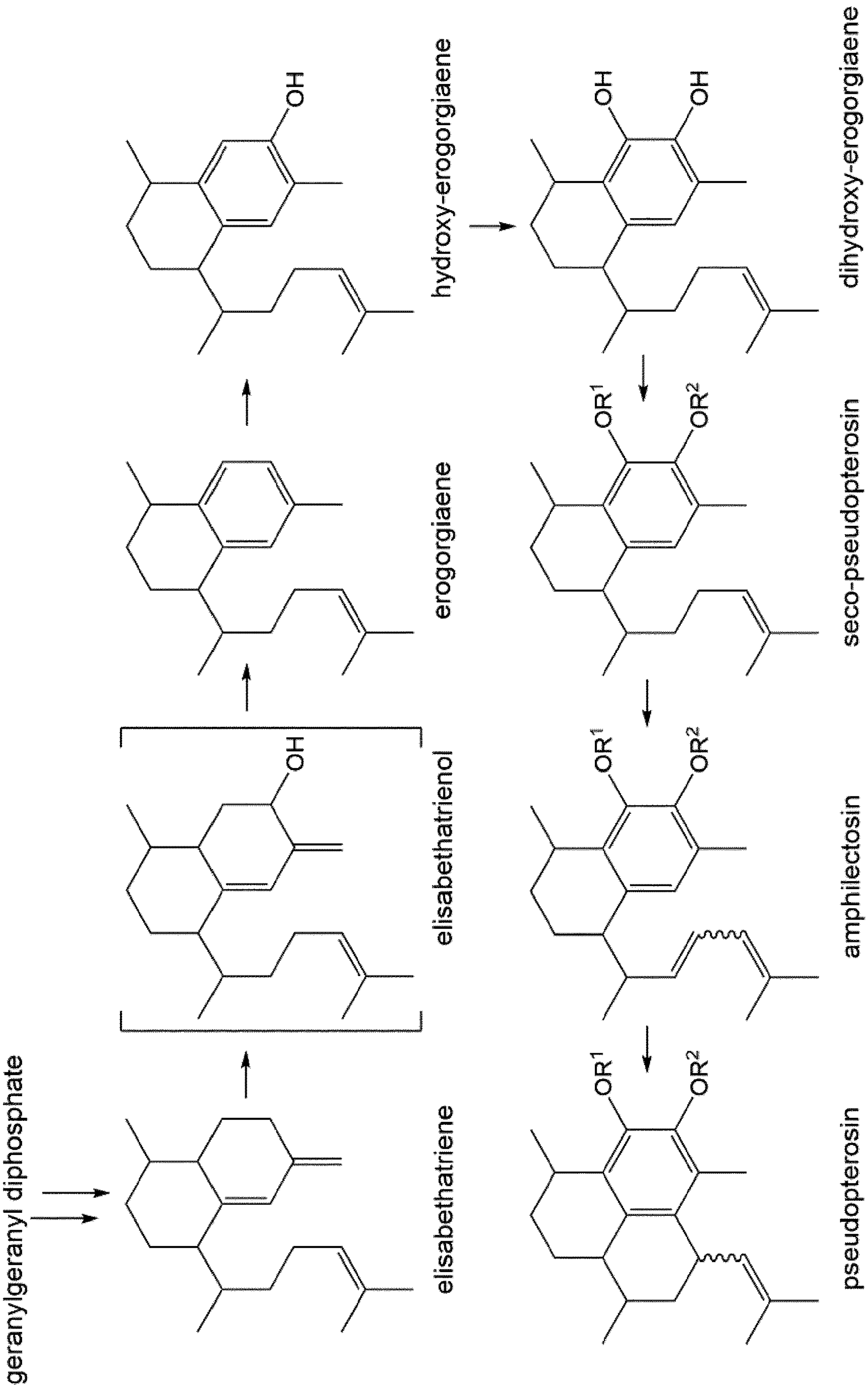
FIG. 9 shows the postulated biosynthetic pathway of pseudopterosin biosynthesis, leading from the geranylgeranyl diphosphate to pseudopterosin via elisabethatrienol and erogorgiaene (R=—H or -sugar).

This mechanistic sequence is supported by detection of elisabethatriene as well as a transient hydroxylated elisabethatriene derivative in crude *A. elisabethae* coral extracts. The spontaneous dehydration of the hydroxylated intermediate to erogorgiaene has been proposed as an essential step in the pseudopterosin biosynthesis (FIG. 9). In analogy, the observed chemo-enzymatic conversion of IE A to (−)-erogorgiaene employs the same mechanism. Since erogorgiaene has potent activity against *M. tuberculosis* (with reported MICs as low as 32.25 μg/ml), the current technology platform can provide a scalable and sustainable access to this interesting natural product. In light of the accelerated evolution of infectious diseases and the lack of new molecular leads for advanced antibiotic therapy, this platform addresses the essential need for preparedness to fight infection epidemics.

REFERENCES

1. Newton, C. G. et al. Pseudopterosin synthesis from a chiral cross-conjugated hydrocarbon through a series of cycloadditions. Nature chemistry 7, 82-86; 10.1038/NCHEM.2112 (2015).
2. Davies, H. M. L. & Walji, A. M. Direct synthesis of (+)-erogorgiaene through a kinetic enantiodifferentiating step. Angewandte Chemie (International ed. in English) 44, 1733-1735; 10.1002/anie.200462227 (2005).
3. Dixit, M., Weitman M., Gao, J., Major, D. T. Chemical Control in the Battle against Fidelity in Promiscuous Natural Product Biosynthesis: The Case of Trichodiene Synthase. ACS Catal. 2017 Jan. 6; 7(1):812-818. doi: 10.1021/acscatal.6b02584.
4. Kohl, A. C., Ata, A. & Kerr, R. G. Pseudopterosin biosynthesis-pathway elucidation, enzymology, and a proposed production method for anti-inflammatory metabolites from *Pseudopterogorgia elisabethae*. Journal of industrial microbiology & biotechnology 30, 495-499; 10.1007/s10295-003-0076-7 (2003).
5. Trott, O. & Olson, A. J. AutoDock Vina: improving the speed and accuracy of docking with a new scoring function, efficient optimization, and multithreading. Journal of computational chemistry 31, 455-461; 10.1002/jcc.21334 (2010).
6. Hirte, M., Meese, N., Mertz, M., Fuchs, M. & Brück, T. B. Insights Into the Bifunctional Aphidicolan-16-ß-ol Synthase Through Rapid Biomolecular Modeling Approaches. Frontiers in chemistry 6, 101; 10.3389/fchem.2018.0010 (2018).
7. Zimmermann, L. et al. A Completely Reimplemented MPI Bioinformatics Toolkit with a New HHpred Server at its Core. Journal of molecular biology 430, 2237-2243; 10.1016/j.jmb.2017.12.007 (2018).
8. Hirte, M. et al. From microbial upcycling to biology-oriented synthesis. Combining whole-cell production and chemo-enzymatic functionalization for sustainable taxanoid delivery. Green Chem 20, 5374-5384; 10.1039/c8gc03126f (2018).

The invention claimed is:

1. A modified terpene synthase comprising at least one modified amino acid residue as compared to an amino acid sequence corresponding to an unmodified wild type terpene synthase according to SEQ ID NO: 1, wherein said at least one modified amino acid residue is located in an α-helix structure being part of, or close to, an active site pocket of the terpene synthase, and wherein said at least one modified amino acid residue is an amino acid with a hydrophobic side chain and/or an amino acid with a polar uncharged side chain;

wherein the modified terpene synthase has at least 95% sequence identity to the unmodified wild type terpene synthase according to SEQ ID NO: 1;

wherein said at least one modified amino acid residue is a substitution of a wild type amino acid residue selected from:

(i) methionine at position 71, (ii) methionine at position 75, (iii) glycine at position 182, (iv) histidine at position 184, (v) methionine at position 300, and (vi) methionine at position 304, in the amino acid sequence of the unmodified wild type terpene synthase according to SEQ ID NO: 1.

2. The modified terpene synthase according to claim 1, wherein the modified terpene synthase catalyzes the production of at least one pseudopterosin intermediate and/or the production of at least one pseudopterosin from Geranylgeranyl pyrophosphate (GGPP) in a host cell in an amount that is greater than the amount of said pseudopterosin intermediate and/or said pseudopterosin produced from GGPP by the unmodified wild type terpene synthase having the amino acid sequence according to SEQ ID NO: 1 in the same host cell and under the same conditions, and/or wherein the modified terpene synthase catalyzes the production of at least one side product from GGPP in a host cell in an amount that is smaller than the amount of said side product produced from GGPP by the unmodified wild type terpene synthase having the amino acid sequence according to SEQ ID NO: 1 in the same host cell and under the same conditions.

3. The modified terpene synthase according to claim 1, wherein the terpene synthase is a Hydropyrene synthase (HpS) comprising the amino acid sequence according to SEQ ID NO: 1.

4. The modified terpene synthase according to claim 1, wherein the modified terpene synthase comprises at least one substitution selected from the group consisting of:

(i) a substitution of methionine for tyrosine at position 71, (ii) a substitution of methionine for phenylalanine at position 75, (iii) a substitution of methionine for leucine at position 75, (iv) a substitution of glycine for alanine at position 182, (v) a substitution of glycine for phenylalanine at position 182, (vi) a substitution of histidine for alanine at position 184, (vii) a substitution of histidine for phenylalanine at position 184, (viii) a substitution of methionine for isoleucine at position 300, (ix) a substitution of methionine for isoleucine at position 304, (x) a substitution of methionine for threonine at position 304, and (xi) a substitution of methionine for cysteine at position 304, in the amino acid sequence of the unmodified wild type HpS according to SEQ ID NO: 1.

5. The modified terpene synthase according to claim 1, wherein the amino acid sequence of said modified terpene synthase further comprises one or more amino acid deletions, substitutions, and/or additions at positions other than at position 71, 75, 182, 184, 300, and/or 304 according to the amino acid sequence of the unmodified wild type terpene synthase according to SEQ ID NO: 1.

6. A modified terpene synthase according to claim 1, wherein said amino acid with a hydrophobic side chain is alanine, valine, isoleucine, leucine, methionine, phenylalanine, tyrosine, or tryptophan, and/or wherein said amino acid with a polar uncharged side chain is threonine, cysteine, asparagine, glutamine, or serine.

7. The modified terpene synthase according to claim 2, wherein said modified terpene synthase catalyzes the production of Elisabethatriene, Isoelisabethatriene A, Isoelisabethatriene B, Erogorgiaene, Seco-Pseudopterosin, and/or Pseudopterosin A.

* * * * *